US006342226B1

(12) United States Patent
Betbeder et al.

(10) Patent No.: US 6,342,226 B1
(45) Date of Patent: Jan. 29, 2002

(54) METHOD FOR INCREASING IMMUNOGENICITY, PRODUCT OBTAINED AND PHARMACEUTICAL COMPOSITIONS

(75) Inventors: Didier Betbeder, Aucamville; Christian Davrinche, Cornebarrieu; Jean-Luc Davignon, Tournefeuille; Eric Prieur, Toulouse, all of (FR)

(73) Assignee: Biovector Therapeutics, S.A., Labege Cedex (FR)

( * ) Notice: Subject to any disclaimer, the term of this patent is extended or adjusted under 35 U.S.C. 154(b) by 0 days.

(21) Appl. No.: 09/221,945

(22) Filed: Dec. 28, 1998

Related U.S. Application Data

(63) Continuation of application No. 08/832,461, filed on Apr. 2, 1997, now abandoned, and a continuation of application No. 08/777,293, filed on Dec. 27, 1996, now abandoned, each is a continuation of application No.08/488,092, filed on Jun. 7, 1995, now abandoned.

(30) Foreign Application Priority Data

Aug. 31, 1994 (FR) .............................................. 94 10479

(51) Int. Cl.$^7$ ............................................ A61K 39/385
(52) U.S. Cl. ............................... 424/196.11; 424/184.1; 424/193.1; 424/194.1; 424/204.1; 424/209.1; 424/278.1; 424/497; 424/498
(58) Field of Search .......................... 424/184.1, 186.1, 424/192.1, 193.1, 194.1, 196.11, 204.1, 210.1, 209.1, 211.1, 497, 498, 278.1

(56) References Cited

U.S. PATENT DOCUMENTS 5,151,264 A     9/1992    Samain et al.
5,891,475 A  *  4/1999    Perrin et al. ................. 424/498
6,090,406 A  *  4/1999    Popescu et al. .............. 424/450

FOREIGN PATENT DOCUMENTS

| EP | 0 344 040 | 11/1989 | |
| EP | 352 295 | 1/1990 | |
| FR | WO 94/23701 | * 10/1994 | ............ A61K/6/16 |
| WO | WO96/06638 | 3/1996 | |

OTHER PUBLICATIONS

N.van Rooijen "Liposomes", Encyclopedia of Immunology, I.M. Roitt et al., Academic Press, London, pp. 986–988, 1992.

"Expression of Human Cytomegalovirus Immediate Early Protein, IE1 In Insect Cells: Splicing of RNA and Recognition by CD4+ T–Cell Clones", Biochemical and Biophysical Research Communications, vol. 195, No. 1, C. Davrinche et al., pp. 469–477, Aug. 31, 1993.

* cited by examiner

*Primary Examiner*—Donna C. Wortman
*Assistant Examiner*—Robert A. Zeman
(74) *Attorney, Agent, or Firm*—Hoffmann & Baron, LLP; Irving N. Feit

(57) ABSTRACT

The present invention relates to a method for increasing the immunogenicity of an antigen, characterized in that the antigen is combined via stable interactions with a particulate vector, said vector containing:

a non-liquid hydrophilic core, and, optionally;

an outer layer of compounds chosen from the group comprising phospholipids and fatty acids.

The present invention also relates to a product thereby obtained and to a pharmaceutical composition containing such product.

29 Claims, 16 Drawing Sheets

Figure 2:
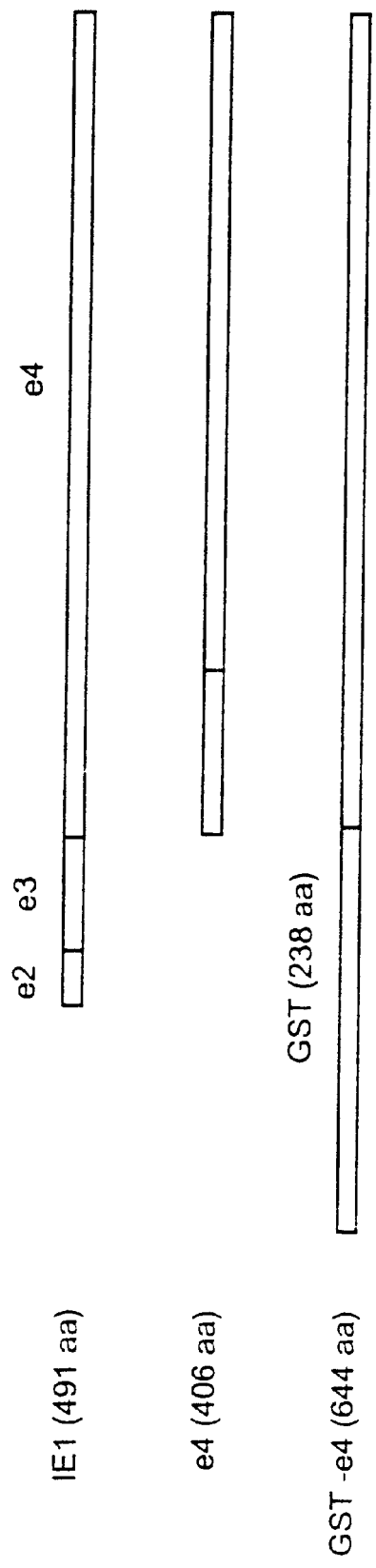

FIG. 2 DIAGRAM OF THE PROTEIN IE1 OF THE HUMAN CYTOMEGALOVIRUS, OF THE POLYPEPTIDE e4 AND OF THE FUSION PROTEIN GST-e4 (82 kDa).

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

CCCGGGAATT CTCATGGTCA AACAGATTAA GGTTCGAG      38

(2) INFORMATION FOR SEQ ID NO:2:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CCCGGGAAGC TTTTACTGGT CAGCCTTGCT TCTA      34

METHOD FOR INCREASING IMMUNOGENICITY, PRODUCT OBTAINED AND PHARMACEUTICAL COMPOSITIONS

This application is a continuation of Ser. No. 08/777,293 filed Dec. 27, 1996, abandoned, and of Ser. No. 08/832,461 filed Apr. 2, 1997, abandoned, both of which are continuing applications of Ser. No. 08/488,092 filed Jun. 7, 1995, abandoned, which asserted the Aug. 31, 1994 priority date of French application Serial No. 94 10479, all of which applications are incorporated herein by reference.

The present invention relates to a method enabling the immunogenicity of an antigen to be increased, and to the use of products capable of being obtained, in particular as a vaccine.

The human cytomegalovirus (CMV), a herpesvirus in the latent state in immunocompetent individuals, is responsible for a wide variety of pathologies which are often fatal in the case of immunosuppression (foetus, graft, AIDS, leukaemia, cancer) (for review see (1)). CMV is the main source of congenital malformations of infectious origins. For all these reasons, CMV poses a serious public health problem. The battle against this virus is limited to chemotherapy with non-specific antivirals such as Ganciclovir® and Foscarnet®, the side effects and nephrotoxicity of which have been described. As regards prevention, passive immunotherapy (injection of gamma globulins) decreases the incidence of primary infection in seronegative marrow grafts. In transplant patients (marrow, kidney, liver, heart, liver allografts), CMV infection is associated with graft rejection. The recipients, under immunosuppressant (cyclosporin) are treated with Ganciclovir® during transplantation, and receive gamma globulins during the three months following surgery. The intravenous injection of immunoglobulins at high dose in these patients has permitted a reduction in the incidence of pneumonia and rejection in some cases. This gives rise to the not insignificant problem of the very high cost associated with these treatments. Opportunistic CMV infection in HIV+ individuals is among the most dramatic, and necessitates chemotherapy with antivirals.

The economies achieved by elaborating a policy of prevention of diseases associated with CMV infection in individuals at risk would be substantial. In effect, estimates of the cost associated with vaccinating an individual and with covering the attendant expenses (serological analyses, vaccine, treatment of minor side effects), carried out in the United States (2), show that this cost appears to be about 50 times lower than that of the care provided for a newborn infant who is a victim of a congenital infection. CMV infection is observed in ⅔ of renal transplant patients and at a high incidence in other transplant patients. If it is associated with complications in about ⅓ of them, the annual cost added to that of transplantation is considerable. Despite the impact on the disease of drugs such as Ganciclovir® or the injection of gamma globulins, the prevention of the primary infection and of reactivation in these patients should be a priority. The benefits of immunization are obvious from both a clinical and an economic standpoint.

The elaboration of a CMV vaccine should make it possible to curb the development of pathologies associated with congenital infections by vaccinating young women before and during pregnancy, to provide for the protection of patients awaiting transplantation and to initiate an anti-cytomegalovirus response in asymptomatic HIV+ individuals. The use of cured virus does not appear to be suitable, since viral extracts do not in general induce a cytotoxic TCD8+ type response. Attenuated virus gives rise to the problem of the oncogenic character, latency and reactivation of the viral particles. The development of recombinant vaccines which should enable these risks to be avoided necessitates knowledge of the most immunogenic antigens or antigen fragments (epitopes) of the infectious agent. The aim of vaccination is the induction of a protective immunity. Rational approach to vaccination should involve three steps: (i) identification of the effector mechanisms responsible for protection, (ii) choice of an antigen capable of inducing a response in all individuals, and (iii) use of an administration route for the vaccine which is capable of inducing the desired type of response (humoral: antibodies, cellular: cytotoxic and helper).

The body's defence against a viral infection is brought about essentially by the development of a humoral immune response (production of neutralizing antibodies) preventing adsorption of the virus to the cell surface on the one hand, and a cellular response (cytotoxic TCD8+ cells and TCD4+ helper cells) removing infected cells and inhibiting viral replication (synthesis of cytokines (TNFα, IFN-γ, etc.)) on the other hand. As regards human cytomegalovirus, among the 200 proteins encoded by the double-stranded DNA (230 kbp), three of them are the respective major targets of these different types of response: the envelope glycoprotein gB (3), the tegument phosphoprotein pp65 (4) and the regulatory phosphoprotein IE1 (5).

While the elaboration of a CMV vaccine appears to be a necessity, there remains the general problem of the mode of conveying the recombinant antigens. The antigens introduced into synthetic structures must be capable of initiating or restoring a lasting B and T (CD4+ helper and cytotoxic CD8−) immune response, thereby effecting protection of the individuals against a primary infection, a reinfection or a reactivation of the latent virus. The activation of T cells (naive cells or memory cells) is linked to the capacity for presentation of the antigen by the antigen presenting cells, the most important of which are the dendritic cells, B lymphocytes and macrophages. In this context, the vector particles will have to permit access to the endogenous (class I, TCD8+) and exogenous (class II, TCD4+) presentation pathways.

The company Biovector Therapeutics has developed a type of structure called Biovecteur Supramoléculaire [Supramolecular Biovector] consisting of a polysaccharide core (PSC) covered with a surrounding outer layer of fatty acids (AC) or of phospholipids (SMBV), the composition of which can be varied. The polysaccharide mesh possesses an adjustable degree of crosslinking, can be functionalized (anionic or cationic radical), is very stable and permits the binding of a large amount of antigen inside the core as well as at its periphery.

Unexpectedly, the Applicant found that the combination of a protein or peptide with these vectors enabled a potentiation of the immunogenic response to be observed, relative to that brought about by administration of the antigen alone.

Accordingly, the subject of the present invention is a method for increasing the immunogenicity of an antigen, characterized in that the antigen is combined via stable interactions with a particulate vector, said vector containing:

a non-liquid hydrophilic core an outer layer of compounds chosen from the group comprising phospholipids and fatty acids.

Preferably, the core consists of a matrix of naturally or chemically crosslinked polysaccharides or oligosaccharides. According to one of the aspects of the invention, ionic ligands are grafted onto the core, it being possible for this ligand to carry, in particular, a function chosen from the group comprising phosphates, sulphates, carboxylic acids, quaternary ammonium groups, secondary amines and primary amines.

The vectors permitting implementation of the method can be between 10 nm and 5 μm in size, and especially advantageous results are obtained with sizes between approximately 25 nm and 200 nm, in particular of the order of 80 nm.

The combination of an antigen with acylated or phospholipid-containing particulate vectors significantly increases the proliferative response of TCD4+ cell clones in vitro to this antigen, in the presence of isolated peripheral blood leukocytes and B/EBV lymphocytes. The yields of combination of the antigen with the particles are high, and the complexes obtained are very stable in physiological medium. The demonstration of a potentiation of the proliferative T response underlines the exceptional properties of these biovectors and the value of their potential use in vaccination.

These results are not obtained with a simple mixture, without prior interaction, of the antigen and the particulate vector.

The antigen is combined with the particulate vector via ionic and/or hydrophobic bonds.

According to an aspect of the invention, the outer layer of the particulate vector consists of natural fatty acids bound to the core via covalent bonds. According to another aspect, this outer layer consists of natural or synthetic phospholipids.

The subject of the invention is also a product capable of being obtained by the method described, and which comprises a combination potentiating the immunogenicity of an antigen bound via ionic and/or hydrophobic bonds to a particulate vector, the said particulate vector containing
- a non-liquid hydrophilic core, and
- an outer layer, combined with the core via hydrophobic interactions and/or ionic bonds and consisting of lipids compounds chosen from the group comprising phospholipids and fatty acids.

The antigen can be a protein or peptide of bacterial or viral origin, or a fragment derived from these antigens.

More especially, the invention relates to a product potentiating immunogenicity, as defined above, in which the antigen is a protein of CMV or a fragment of such a protein.

The exceptional properties of these vectors can, in effect, be exploited for the encapsulation of antigens of human CMV, with the aim of designing a recombinant vaccine which would combine the IE1, pp65 and gB antigens for the reasons mentioned above. Such a product would be capable of generating a humoral and cytotoxic response.

The antigen can hence be, in particular, the protein IE1 of CMV, or a fragment of this protein.

A fragment of the recombinant viral protein IE1 of human cytomegalovirus (Towne strain) was produced and purified in the form of a fusion protein (GST-e4) in *E. coli*. The combination of the protein with different types of particle (PSC, AC and SMBV) 80 nm in size is very stable and the yields are very high. We have described an adjuvant effect of the antigen (Ag)/particle complexes on the proliferative response of specific TCD4+ clones in vitro. This effect was observed using peripheral blood leukocytes and EBV-transformed B lymphocytes (B/EBV) as antigen presenting cells.

The proliferation of anti-IE1 T clones in the presence of recombinant GST-e4, soluble or combined with particles, suggests that coupling of the viral antigen to the bacterial GST, the absence of phosphorylation of the protein in this prokaryotic expression system and the combination with biovectors have had no influence on the nature of the peptide epitopes generated by the presenting cells. One of the hypotheses, by which the Applicant in no way intends to limit the invention, is that the adjuvant effect observed when the antigen is combined with the particles might be correlated with a larger uptake of protein by the presenting cell than when the antigen is soluble, as has been found by the Applicant. The concentration of the antigen in the endolysosomal compartments might favour the interaction of class II molecules with viral peptides rather than with endogenous or exogenous peptides originating from serum proteins, for example. The outcome of this would be the expression of a larger number of DR-peptide IE1 complexes at the cell surface. The potentiating effect observed with ACs might be linked to a better accessibility of the antigen. The vectors we used enabled a large mass of antigen to be incorporated by simple mixing in aqueous solution. This represents a considerable advantage relative to the protocols for encapsulation in other types of particle such as liposomes (6).

It is possible that the observed adjuvant effect might also be mediated by an opsonisation of the particles, involving interaction between serum IgGs or complement fragments such as C3b and their respective receptors at the surface of the presenting cells.

The Applicant has shown that a fusion protein which is more stable than e4 alone, between the fragment e4 of CMV and glutathione S-transferase (GST), prepared by genetic engineering, may be used in the vectors according to the invention without necessitating a cleavage step in order to remove the GST portion. This represents a considerable advance, since such a protein can be readily purified, and the elimination of the cleavage step enables the yield to be increased and its large-scale production to be envisaged.

Hence the subject of the invention is also a fusion protein, characterized in that it comprises the fragment e4 of the protein IE1 of CMV and at least part of the glutathione S-transferase protein.

The aim of vaccination is to induce the maturation of cells involved in the specific removal of a pathogenic agent and to maintain clones of memory cells specific for the target antigens in the circulation and in the secondary lymphoid organs. The important contribution of B cells as antigen presenting cells to the activation of T cells has been reported (7). It has been shown that the B cell is effective in taking up soluble antigens at low concentration by endocytosis only by means of its surface immunoglobulin. Studies designed to target liposomes on B lymphocytes make use of the binding to their surface of monoclonal antibodies (8) designed to interact with the surface immunoglobulins of these cells. Since the incidence of specific B lymphocytes is very low, the effect observed here using particles should enable the specific T response of the complexed antigen to be amplified without the latter undergoing a recognition by specific B lymphocytes. The presentation of an Ag to activated TCD4+ cells induces, besides their proliferation, the secretion of cytokines and the expression of surface molecules which are important for the proliferation and differentiation of B cells to plasma cells secreting antibodies.

According to another aspect, the subject of the invention is a pharmaceutical composition, characterized in that it comprises an antigen combined with a particulate vector according to the specification defined above, dispersed in pharmaceutically acceptable excipients.

Its subject is also a product or a composition as defined above, for their use as a vaccine.

Figure 1:
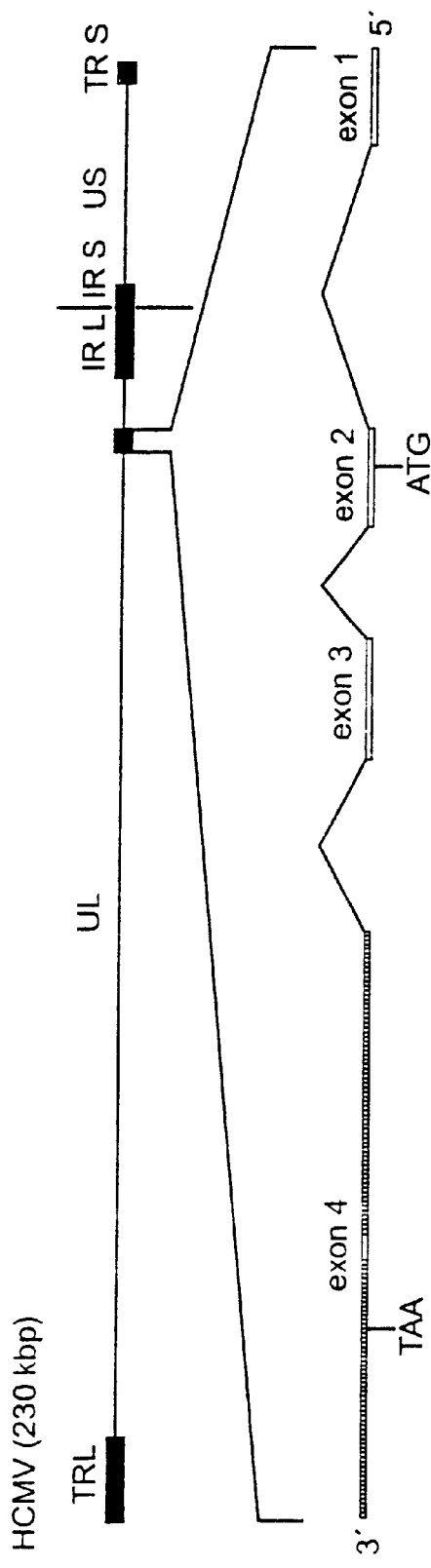

The examples which follow are intended to illustrate the invention without in any way limiting its scope. In these examples, reference will be made to the following figures:

FIG. 1: Diagrammatic representation of the fragment of viral genomic DNA containing IE1 cDNA.

FIG. 2: Diagrammatic representation of the fusion protein GST-e4

Figure 3:
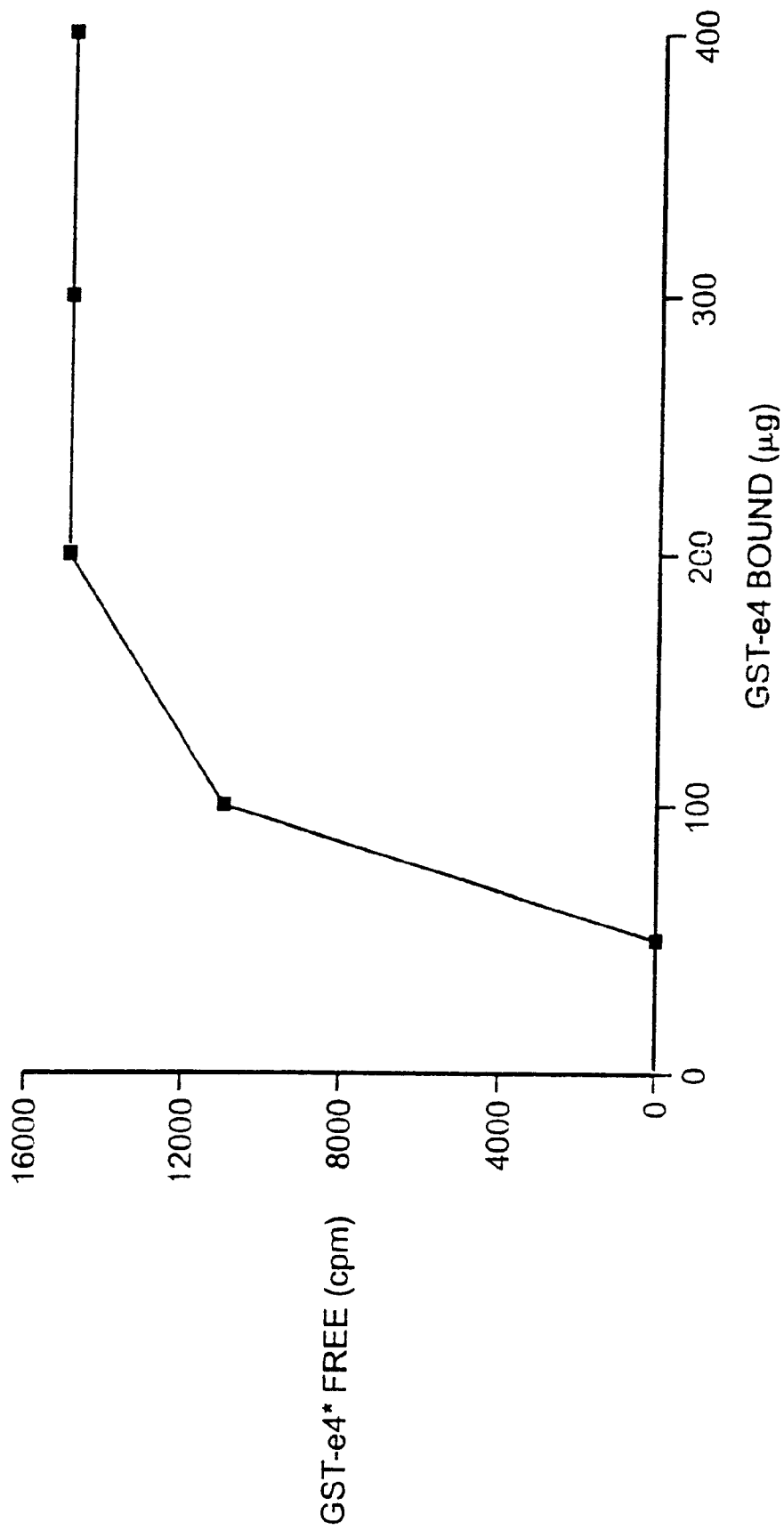

FIG. 3: Curve of saturation of SMBV with purified GST-e4: Increasing amounts of cold GST-e4 (50 to 400 µg) were preincubated with SMBV (100 µg). The complexes thereby formed were incubated in the presence of radiolabelled GST-e4 (GST-e4*), and the degree of combination (cpm) of hot protein was determined by counting after ultrafiltration through Microsep 300.

Figure 4:
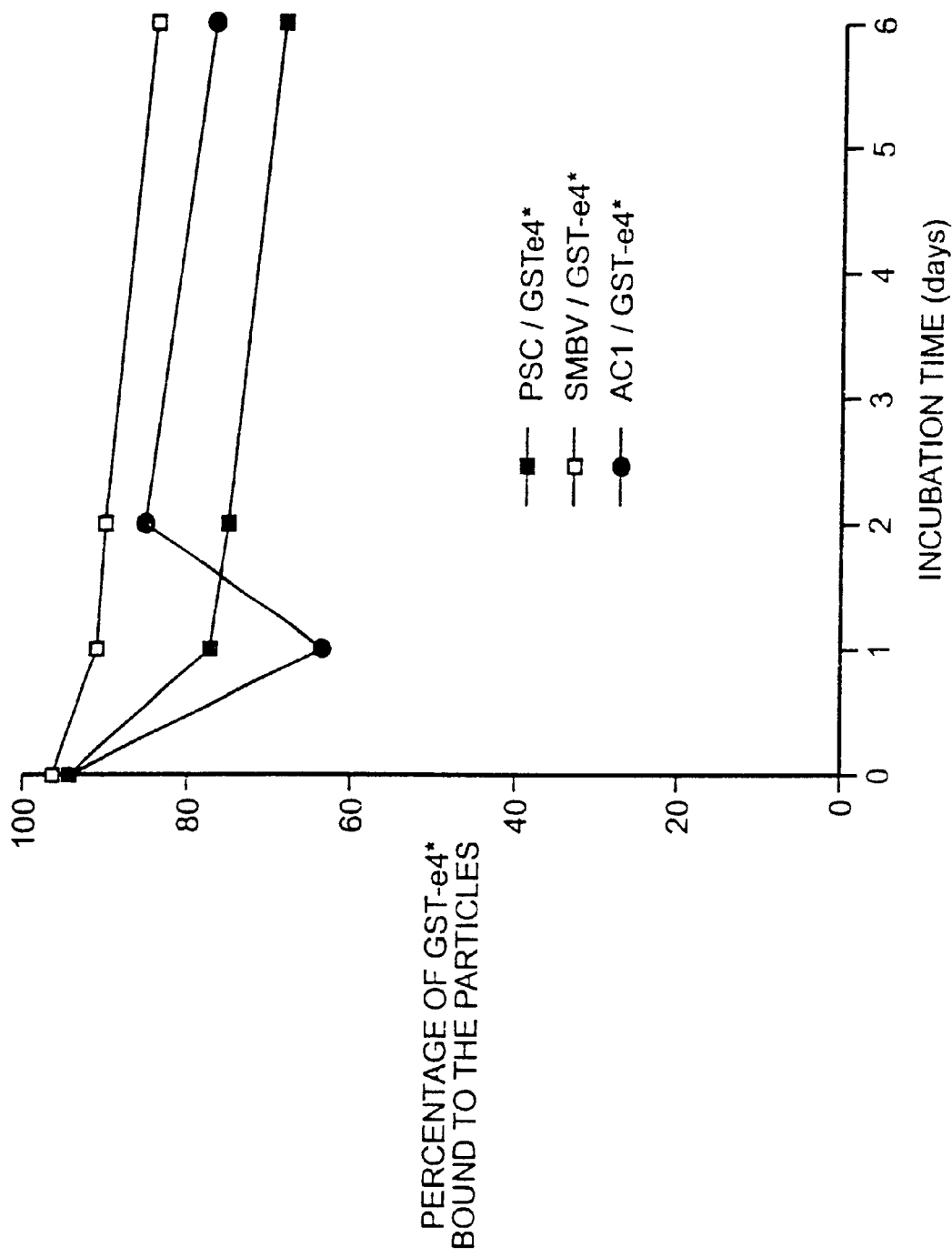

FIG. 4: Stability of the GST-e4/particle combination: The complex GST-e4*/particle complexes were incubated in RPMI/FCS medium at 37° C. for 0 to 6 days. The percentage of GST-e4* combined at the end of each incubation period was determined by counting after ultrafiltration.

Figure 5A:
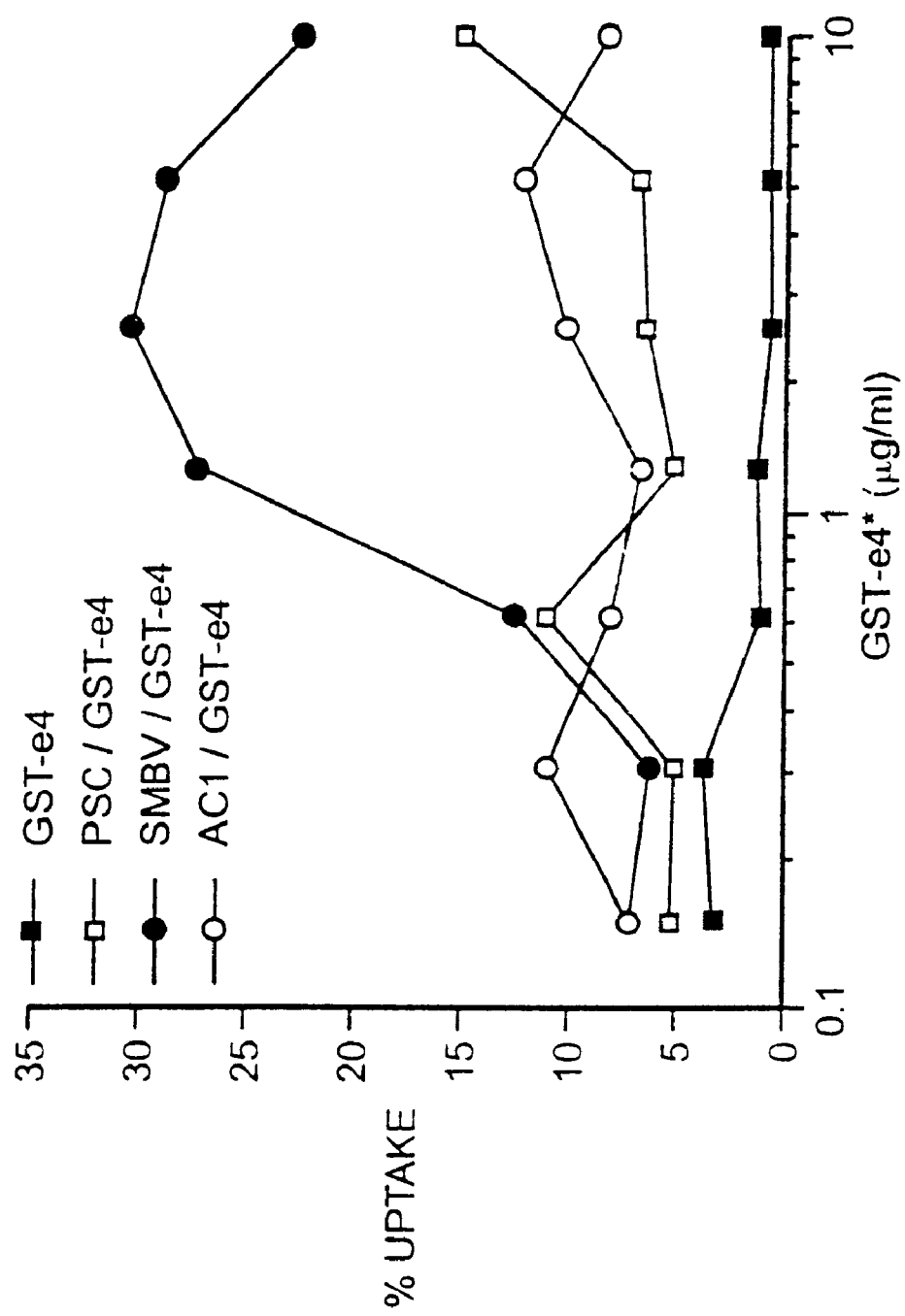
Figure 5B:
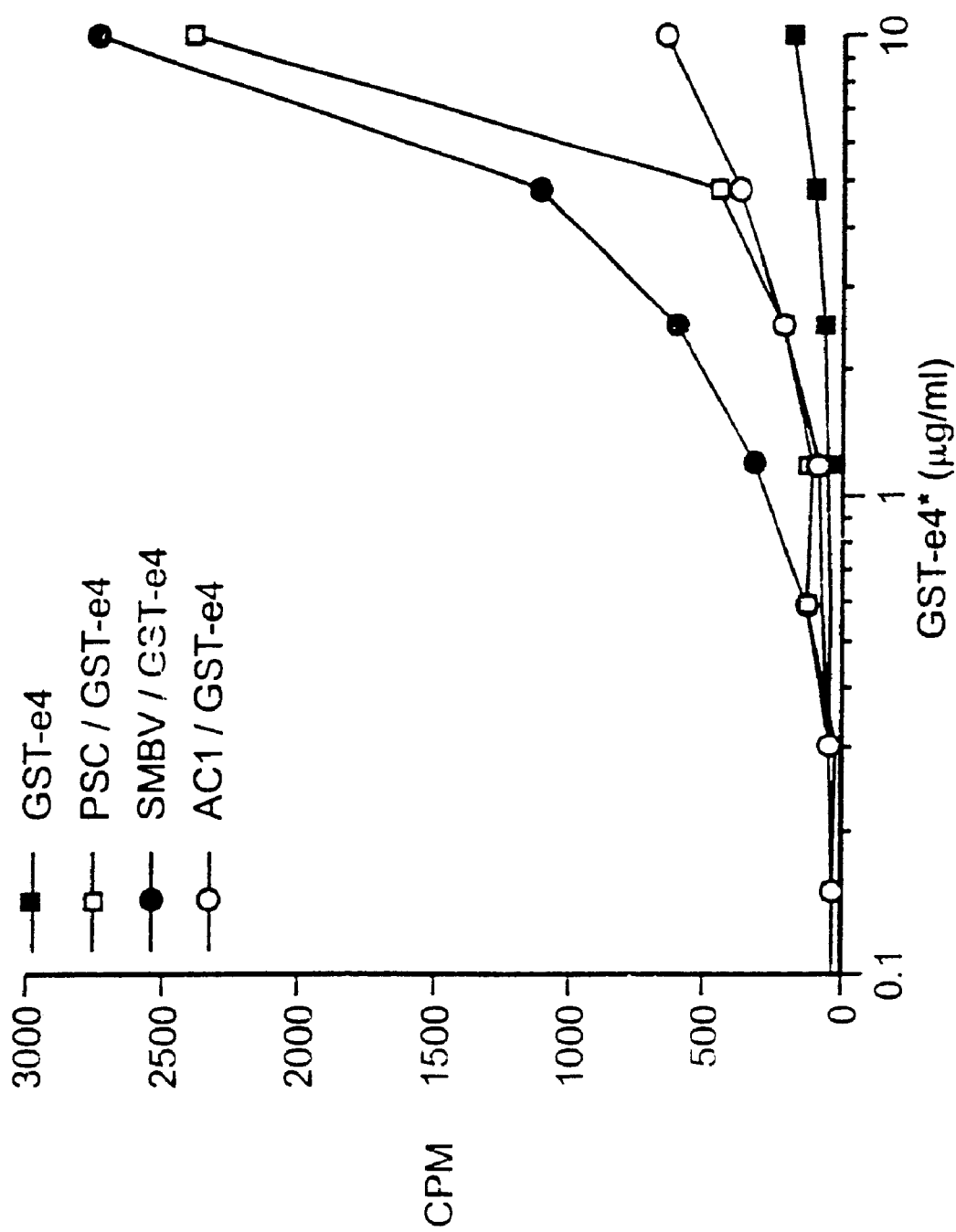
Figure 5C:
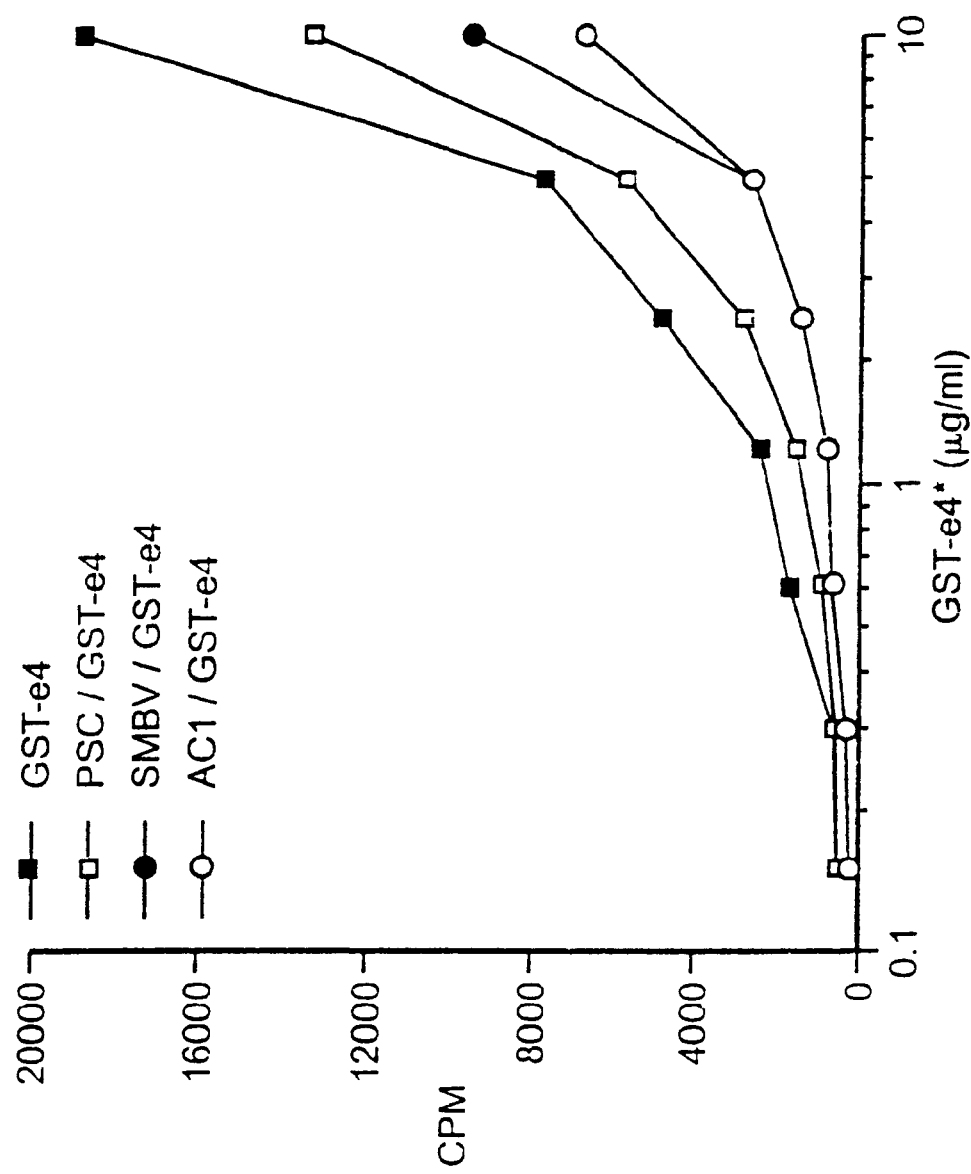

FIGS. 5A, 5B, and 5C: Uptake of GST-e4*, soluble or combined with particles, by B/EBV lymphocytes: The radioactive antigen GST-e4*, free or combined with particles (PSC, AC, SMBV), was incubated in the presence of $5 \times 10^5$ B/EBV lymphocytes in RPMI/FCS at 37° C. for 15 h. The percentage uptake (A), the amount of antigen combined with the cells (B) and the amount of antigen appearing in the medium (C) are shown as a function of the protein concentration in the wells.

Figure 6A:
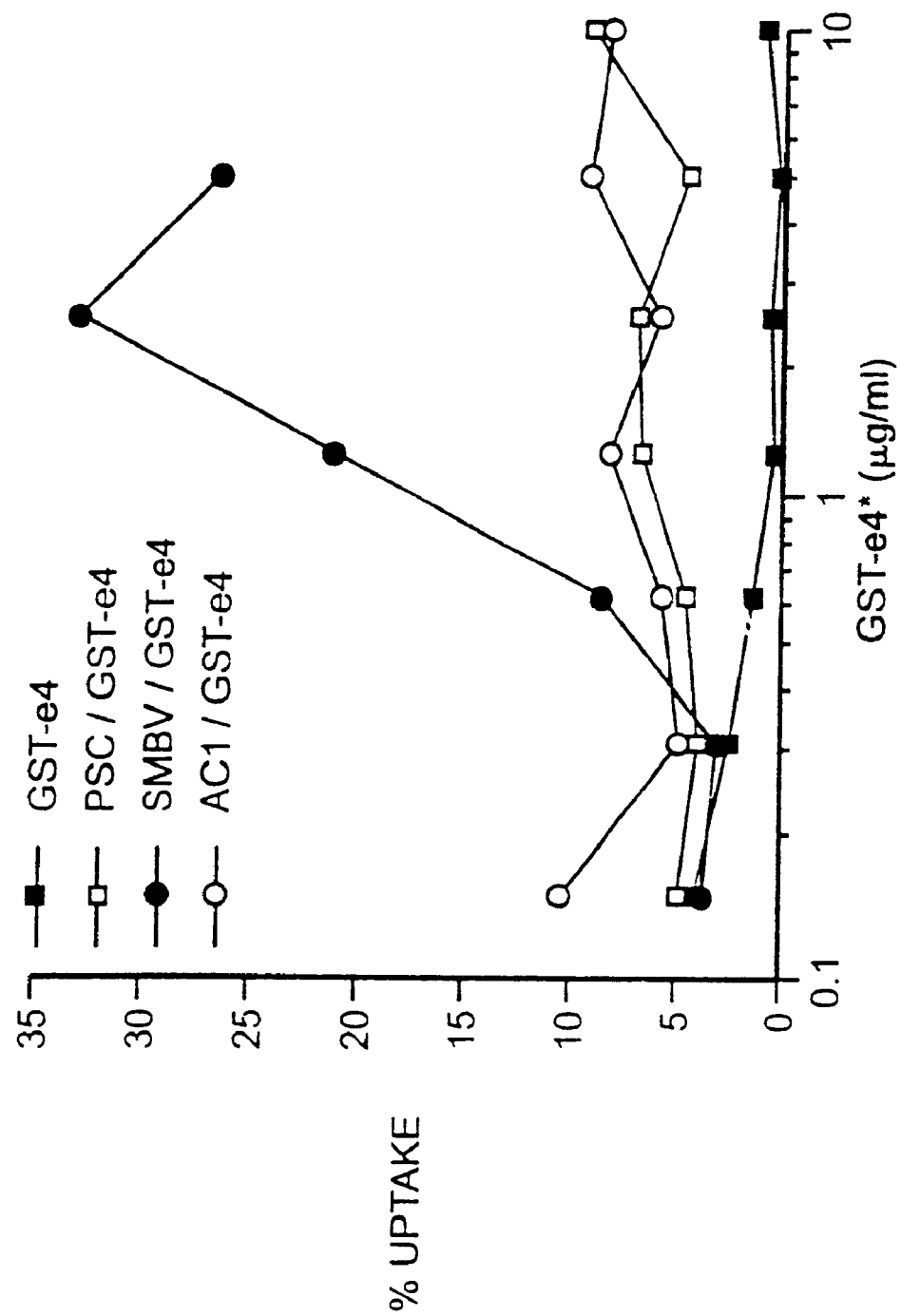
Figure 6B:
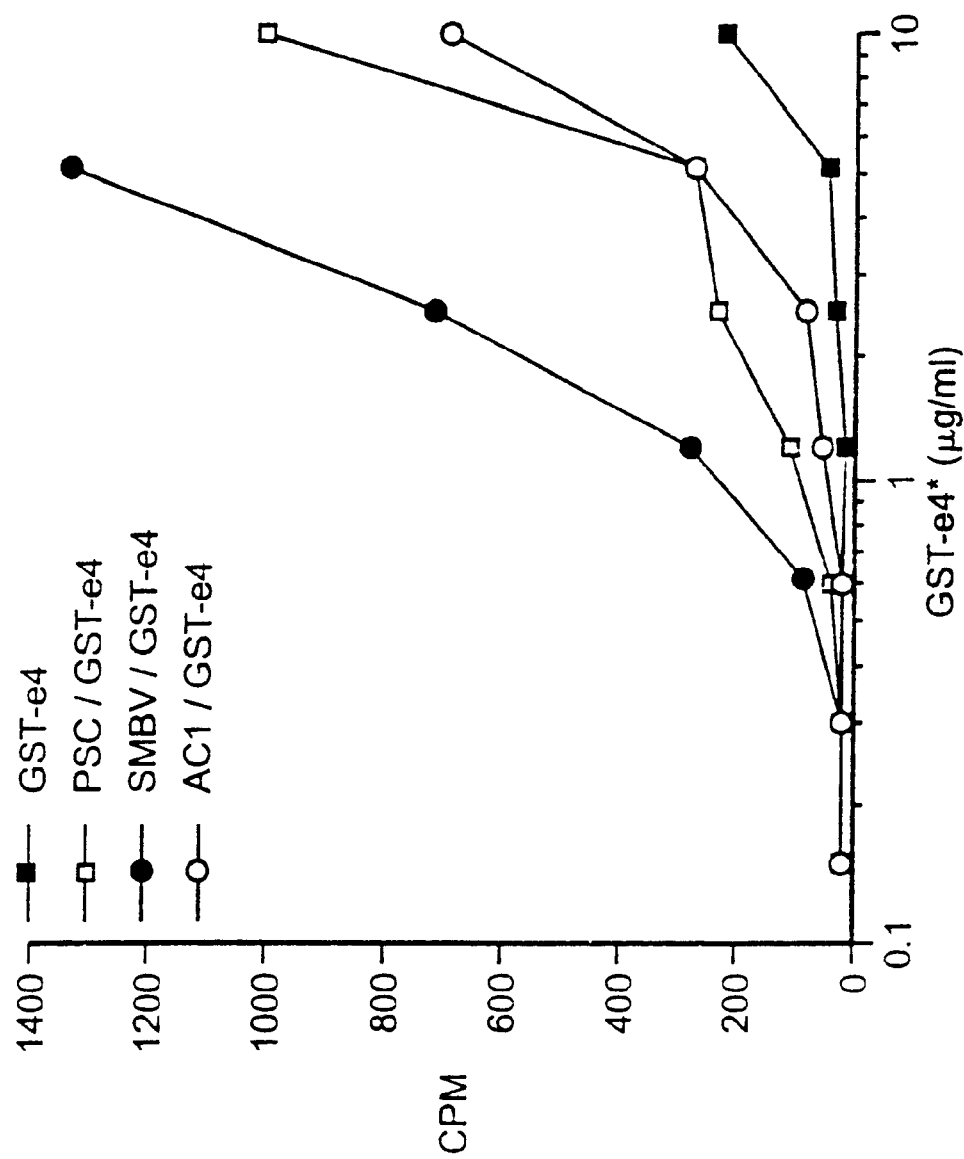
Figure 6C:
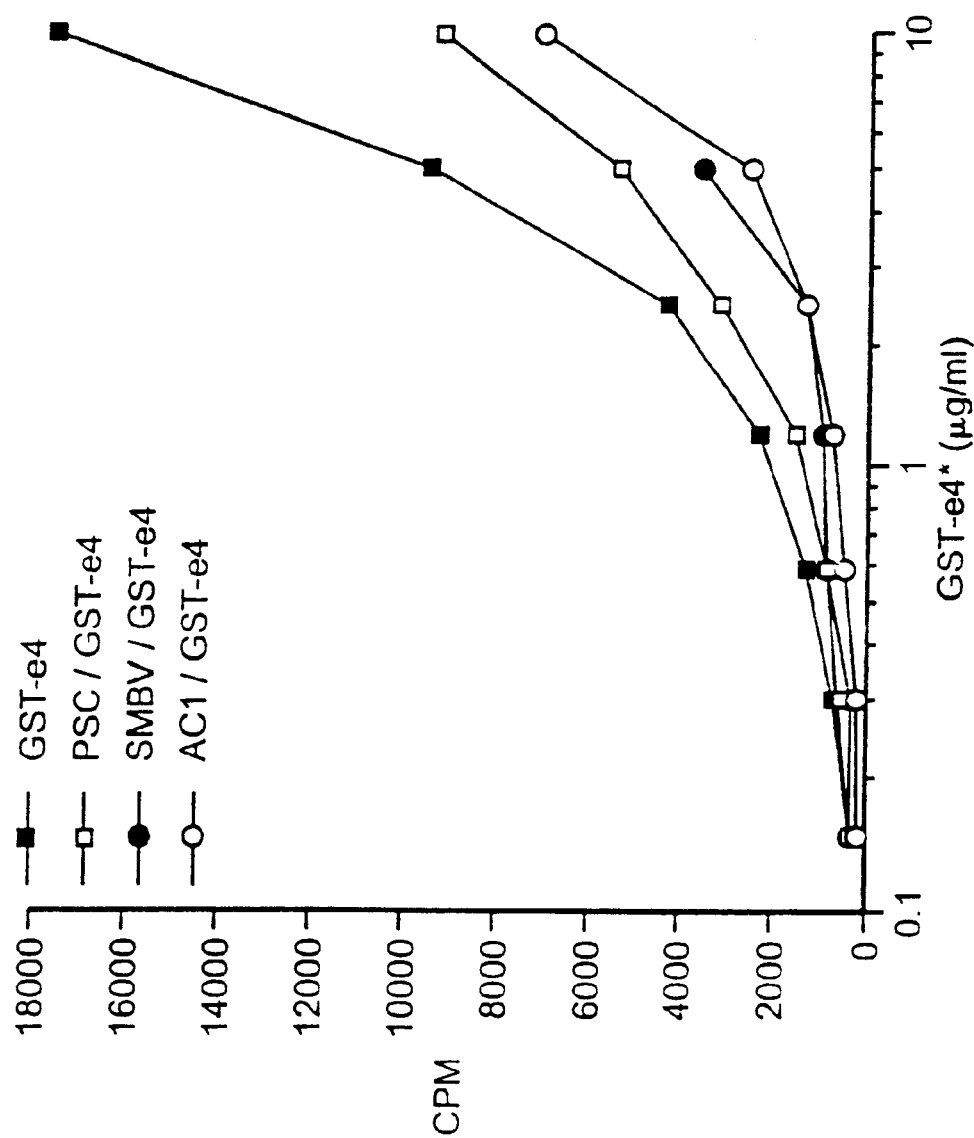

FIGS. 6A, 6B, and 6C: Uptake of GST-e4*, soluble or combined with particles, by the macrophage line "Mono Mac 6": The radioactive antigen GST-e4*, free or combined with particles (PSC, AC, SMBV), was incubated in the presence of $5 \times 10^5$ Mono Mac 6 cells in RPMI/FCS at 37° C. for 15 h. The percentage uptake (A), the amount of antigen combined with the cells (B) and the amount of antigen appearing in the medium (C) are shown as a function of the protein concentration in the wells.

Figure 7:
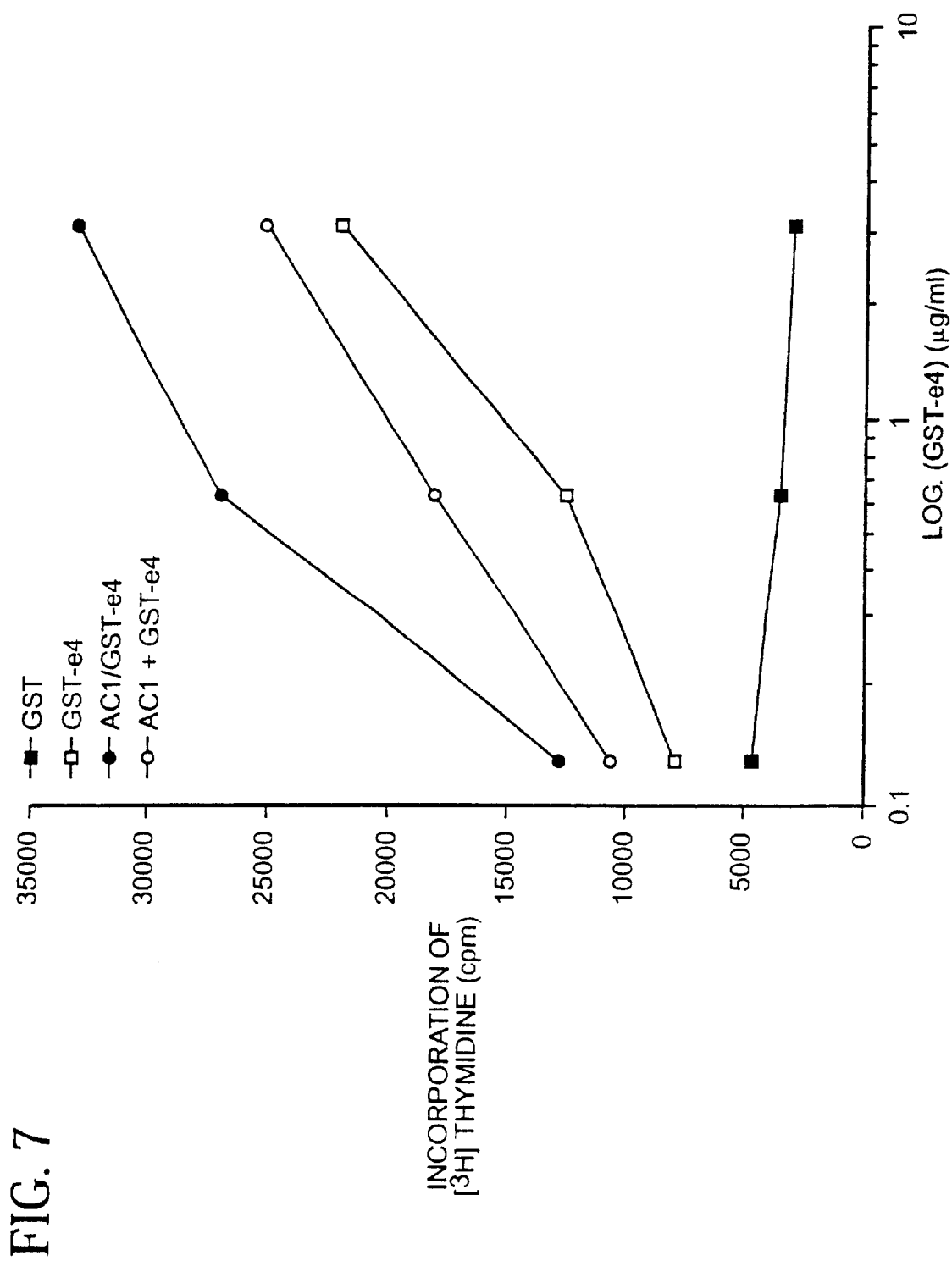

FIG. 7: Test of proliferation of the clone (A3) in the presence of B/EBV lymphocytes and an empty AC/GST-e4 mixture: Clone A3 cells were incubated in the presence of irradiated B/EBV lymphocytes and soluble antigen, alone (GST, GST-e4) or with empty ACs (AC+GST-e4), and with the antigen combined with ACs (AC/GST-e4). The proliferation is determined by the incorporation of [3H]thymidine, measured in cpm.

Figure 8:
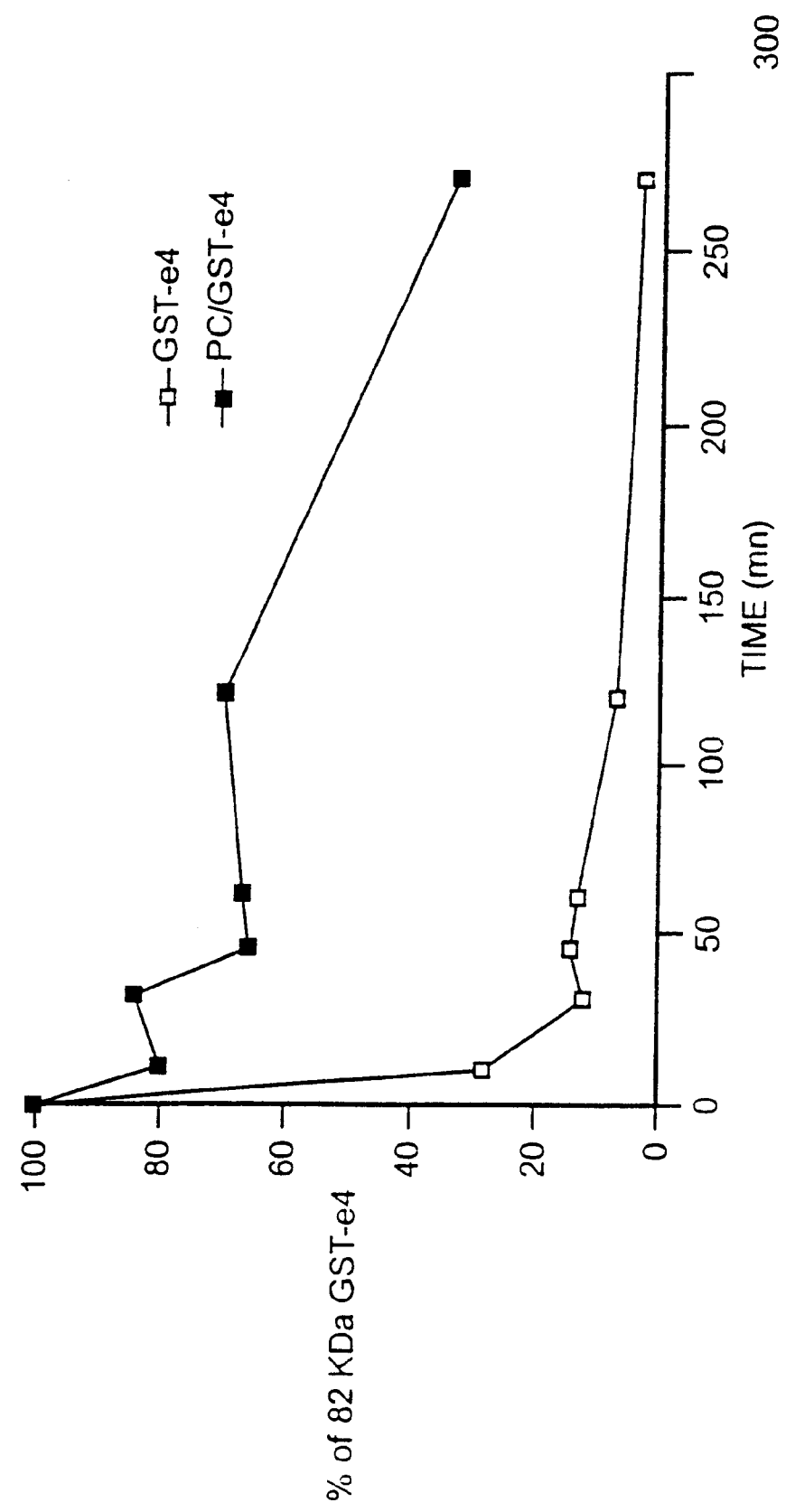

FIG. 8: GST-e4 was protected from proteolysis through its binding to biovectors. Free or PC-associated GST-e4 was incubated with trypsin (1/600 mass ratio) and the reaction was stopped as indicated. Samples were submitted to SDS-PAGE and the 82 kDa GST-e4 was quantified by densitometric scanning of the gel. Results were expressed as the percentage of starting GST-e4.

Figure 9A:
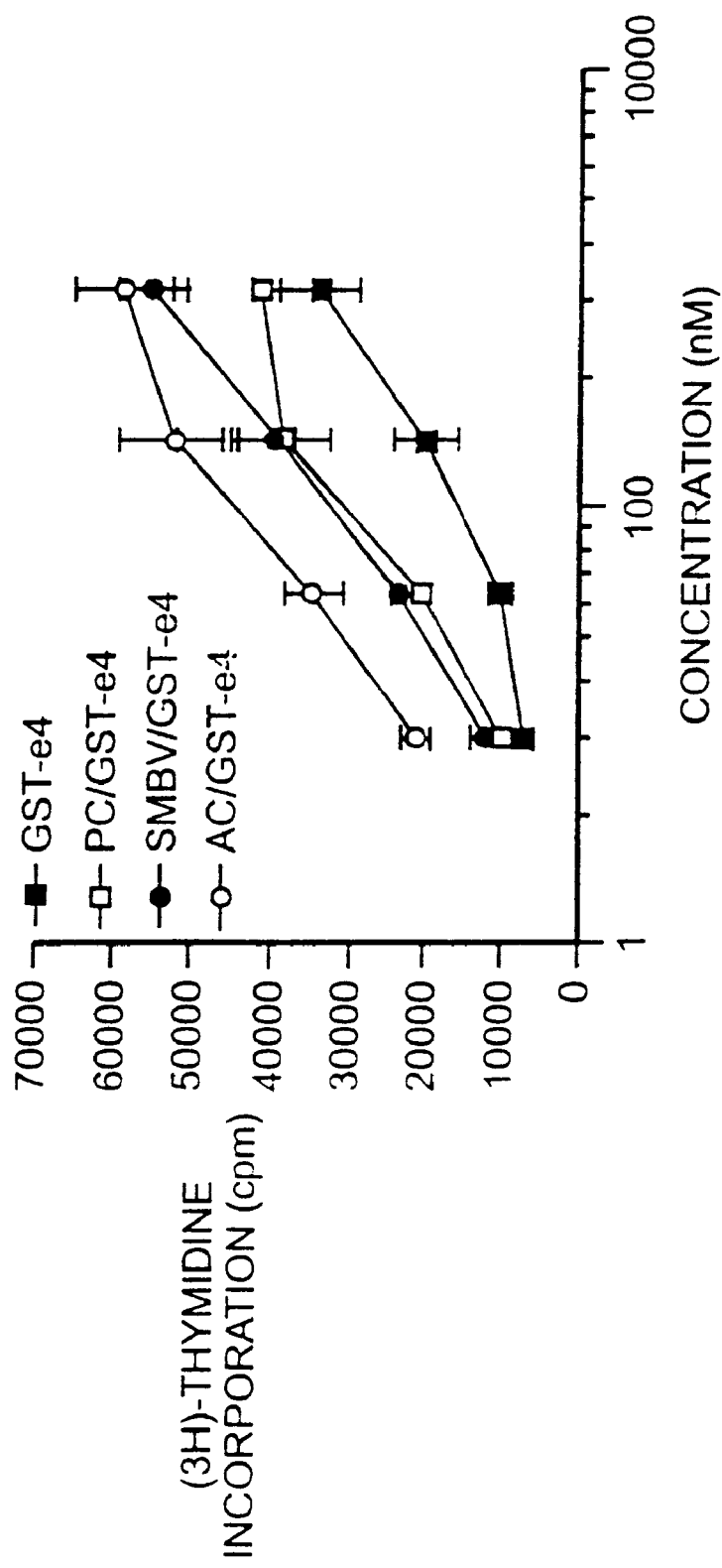
Figure 9B:
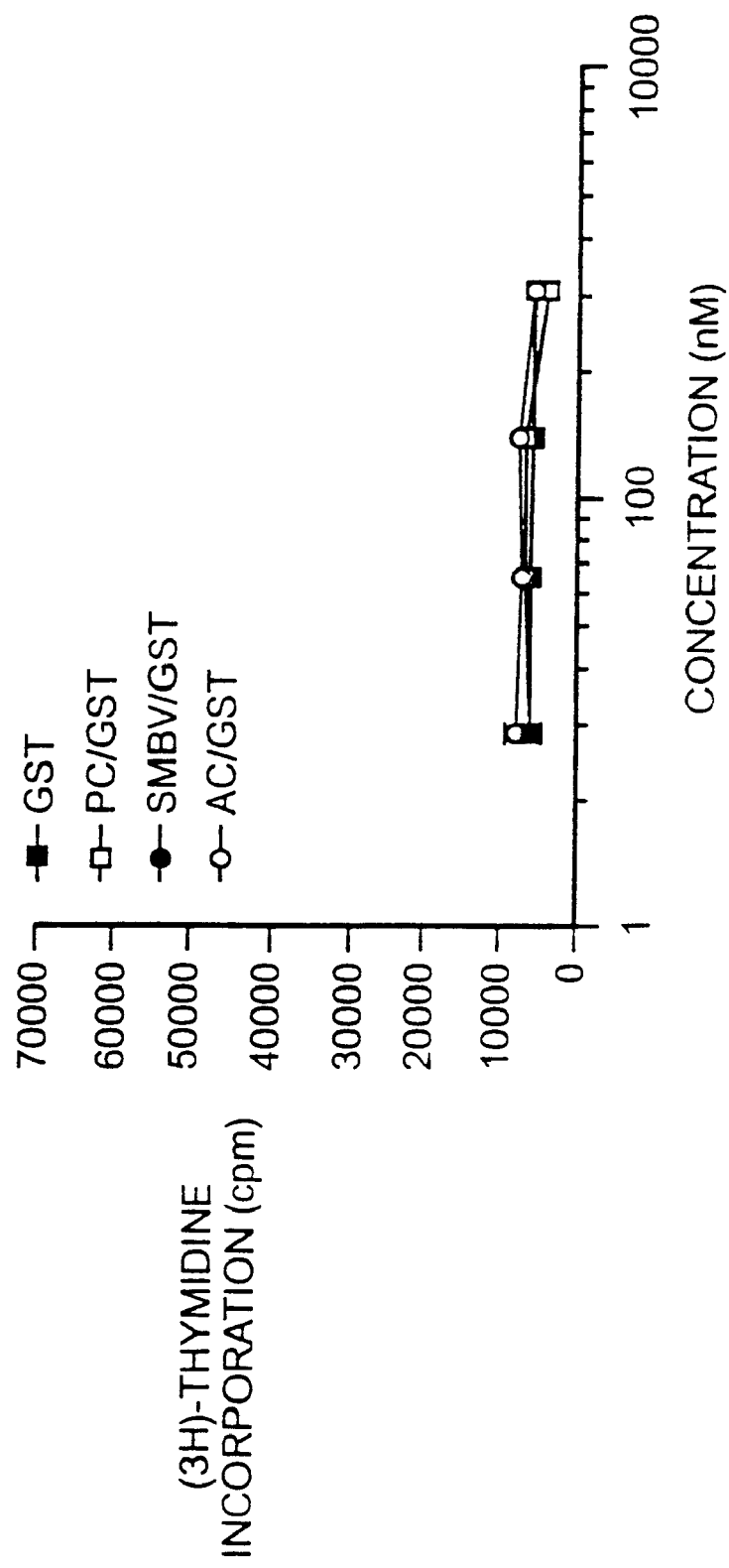

FIGS. 9A and 9B: CD4+ T cell response to GST-e4 was enhanced in vitro after its binding to biovectors with PBL as APC. Cells from clone "BeA3" were cultured in the presence of irradiated PBL and various concentrations of GST-e4 (A) and GST (B) either free or particulate.

Figure 10A:
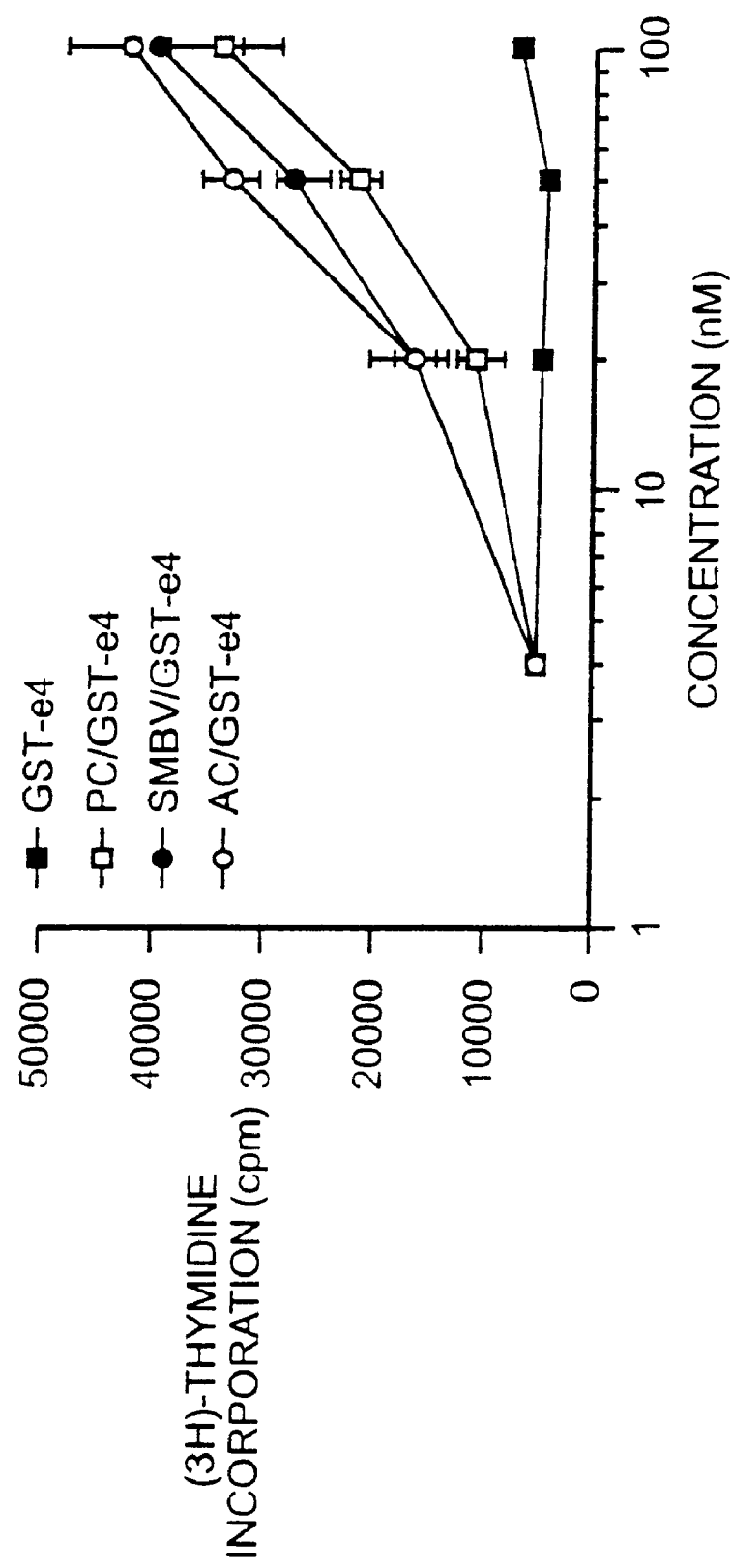
Figure 10B:
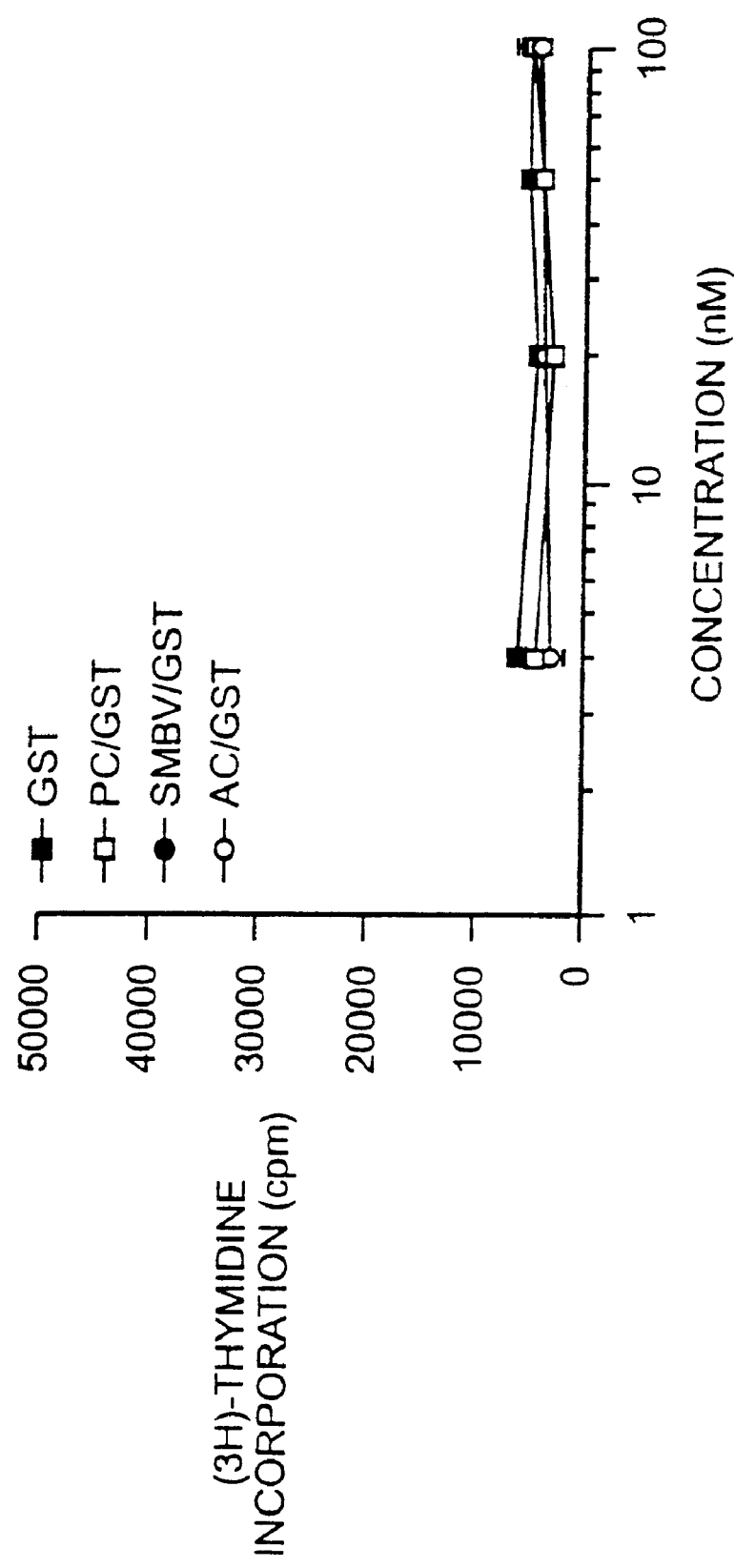

FIGS. 10A and 10B: CD4+ T cell response to GST-e4 was enhanced in vitro after its binding to biovectors with EBV transformed B-cells as APC. Cells from clone "BeA3" were cultured in the presence of irradiated EBV transformed B-cells and various concentrations of GST-e4 (A) and GST (B) either free or particulate.

EXAMPLES

1) Materials and methods

Synthesis of cationized vectors 80 nm in size:

The vectors used in this study were all derived from the same polysaccharide core synthesized from the same batch (PSC). These PSCs were either acylated with palmitic acid (AC) or coated with phospholipid using different types of phospholipids (SMBV).

Synthesis of PSCs 100 g of maltodextrin (Glucidex 6, Roquettes), complying with the maltodextrin monograph in US Pharmacopeia NF XVII, were dissolved in 17 ml of water with vigorous mechanical stirring and thereafter transferred to a glass reactor, into which 2.4 g of NaBH4 were then added. Half an hour later, 44 ml of 10 N sodium hydroxide were added, followed by 9.72 ml (0.124 mol) of a crosslinking agent, epichlorohydrin (Fluka). After 90 min of reaction at room temperature, 31.18 g of a cationizing agent, hydroxycholine (glycidyltrimethylammonium chloride, Fluka), previously dissolved in 20 ml of water, were added. Incubation was maintained for 20 h with mechanical stirring. The gel obtained was diluted with 1.5 l of water and then neutralized with acetic acid. The gel was then milled in a homogenizer by extrusion under high pressure and then ultrafiltered through a 40 kDa filtering module. Ultrafiltration was stopped when the ultrafiltrate no longer reacted with silver nitrate. Analysis of the size of the nanoparticles (PSC) was performed with a Coulter N4SD Nanosizer.

Synthesis of acylated cores (AC)

9.34 ml of palmitoyl chloride were added to 10 g of freshly lyophilized PSCs previously dispersed in 100 ml of dichloromethane (distilled immediately before use). Reaction was continued for 4 hours at room temperature. After the addition of 200 ml of diethyl ether to the reaction medium, the ACs were filtered off on a Büchner, washed with ethanol, taken up in 500 ml of water and homogenized.

Synthesis of SMBV

The PSCs were coated with phospholipid (20% w/w of lyophilized PSCs) using different proportions of phospholipids.

In vivo toxicity tests

The vectors tested (PSC, AC, SMBV) were resuspended in water at a concentration of 1 mg/ml. The pyrogenicity of the samples was determined in vivo in rabbits at a dose of 100 µg of vector per dose according to the European Pharmacopoeia.

Production of the fusion protein GST-e4 in *Escherichia coli*:

Cloning in *Escherichia coli*:

The cDNA corresponding to exon 4 (e4, FIG. 1) was obtained by amplification (PCR) using Taq polymerase (Proméga, Coger, France) from the plasmid pRL 103 (gift of R. LeFemina, (9)) containing the IE region of CMV (Towne strain). The primers A1 (A1=5'CCCGGG✶AATTCTCATGGTCAAA CAGATTAAGGTTCGAG3') (SEQ ID NO. 1) and A2 (A2=5'CCCGGGA⊖AGCTTTTACTGG TCAGCCTTGCTTCTA3') (SEQ ID NO. 2) corresponding, respectively, to the 5' and 3' ends of e4 were used. EcoRI (✶) and Hind III (⊖) sites were introduced into these primers to permit insertion of the PCR fragment into the plasmid pGEX-KG (10). The inserted fragment is in the frame with the glutathione S-transferase (GST) gene, the promoter of which is inducible with isopropyl thiogalactoside (IPTG, Sigma, France). Between the 3' end of the GST gene and the multiple cloning site there lies a region coding for a thrombin-specific peptide cleavage site. The transformation of Escherichia coli DH5α bacteria (Gibco, Cergy, France) and the screening of the recombinants were performed according to standard techniques (11). The insertion of the PCR product corresponding to exon 4 into pGEX-KG was verified by analysis on several clones of the plasmid DNA restriction fragments visualized after electrophoresis on agarose gel containing 1% of ethidium bromide (ETB). The insertion into pGEX-KG was confirmed by testing for the expression of GST-e4 recombinant product after induction with IPTG. Positive clones were sequenced according to Sanger's technique (12) with a "Hot tub sequenase" kit (Pharmacia, Saint Quentin Yvelines, France) according to supplier's directions.

Expression and purification of GST-e4:

Recombinant bacteria stored at −80° C. were cultured in "Luria broth" medium (Difco, Osi, France) containing 50 μg/ml of ampicillin (LG/Ap) (Sigma). This preculture, diluted to 1/10 in LB/Ap, was cultured under the same conditions to OD/600 nm=1.0. Induction of the expression of the GST-e4 recombinant product was carried out by adding 100 μM IPTG to the culture. Incubation was continued for 2 hours at 25° C. to avoid the formation of inclusion bodies (13). The bacteria were harvested by centrifugation and washed in PBS (phosphate buffered saline, pH 7.3, 4.3 mM $Na_2HPO_4$, 1.4 mM $KH_2PO_4$, 137 mM NaCl, 2.7 mM KCl). The cell pellet, stored overnight at −80° C. and then thawed, was taken up in 50 ml of lysis buffer (PBS, 1 mg/ml lysozyme, 1 mM phenylmethylsulphonyl fluoride (PMSF)). The suspension was incubated for 30 minutes in ice and then sonicated. The lysate was stirred for 30 minutes at room temperature in the presence of Triton X-100 (final concentration: 1%) and then clarified by centrifugation (30,000 g/1 h). The supernatant was applied to an affinity column grafted with the GST subtrate (14) (Glutathione/Sepharose 4B, Pharmacia) previously equilibrated in PBS. After the column was washed with PBS, the GST-e4 fusion protein was eluted with 10 mM reduced glutathione in the elution buffer 50 mM Tris-HCl, pH 8.0.

Metabolic labellings of GST-e4 were carried out by adding to the culture medium, and in the proportion of 10 μCi/ml, L-[$^{35}$S]methionine and -cysteine residues (35S Express, NEN, Les Ulis, France) at the time of induction with IPTG. Purification of the radioactive product (GST-e4*) was carried out under the same conditions as for the non-radiolabelled product. The concentration of the purified products was determined by the Bradford method ("Bio-Rad Protein assay" kit, Biorad, Yvry sur Seine, France). Production of the GST-e4 fusion protein was monitored by 10% polyacrylamide gel electrophoresis in the presence of SDS (SDS-PAGE) (15). Precoloured molecular weight markers (Gibco) were used. Visualization was performed either by staining the gel with Coomassie blue or by Western blotting (16) after transfer onto a nitrocellulose membrane (Hybond C super, Amersham, Les Ulis, France) as follows. After saturation in "blotto" (PBS, 0.2% NP40, 2.5% skimmed milk), the membrane was incubated for 1 hour with the immune serum of an individual who was seropositive CMV (CMV+) or with the rabbit antipeptide 85.75 recognizing an epitope located in the C-terminal portion of exon 4 (gift of J. A. Nelson, (17)). The immune serum and the antipeptide were diluted to 1/100 and 1/500, respectively, in "blotto". The membrane was washed 3×5 minutes in PBS and incubated for 1 hour with peroxidase-labelled goat anti-(human Ig) or anti-(rabbit Ig) IgG (GAH/PO, GAR/PO, Nordic, Tebu, Le Perrey en Yvelines, France) diluted to 1/500 in "blotto". After 3 washes of 5 minutes each in PBS, the membrane was incubated in the visualizing solution (PBS, 0.5 mg/ml diaminobenzidine (DAB), 0.1% $H_2O_2$). When the products analysed were radiolabelled, autoradiography of the gel or membrane after Western blotting was carried out on Kodak X-OMAT film (Polylabo, France).

Combination of GST-e4* with the particles:

The GST-e4* fusion protein, dissolved in elution buffer 50 mM Tris-HCl, pH 8.0, was incubated with the three main types of particles (PSC, AC, SMBV) suspended in water, at a concentration of 1 mg/ml. Incubation was performed at 4° C. with stirring for 1 hour. The percentage combination was determined by measuring the radioactivity bound to the particles. Free antigen was removed by ultrafiltration at 5000 g through a membrane having a cut-off threshold of 300 kDa (Microsep 300, Filtron, Coignieres, France). Measurement of the free radioactivity in the eluate and in the washes and the radioactivity bound to the particles was carried out three times on a β counter (BETAmatic, Kontron). The percentage combination was calculated by working out the ratio of the bound radioactivity to the sum of the free radioactivity and the radioactivity bound to the particles. Experiments on combination of GST to the particles were carried out under the same conditions as with GST-e4*. The combination of GST with the particles after washing was confirmed in SDS-PAGE.

Stability of GST-e4* combined with the particles:

The combination of GST-e4* with the three types of particles was performed as above with a GST-e4*/particle ratio of 0.1 (R=0.1). Washes were carried out in RPMI/10% foetal calf serum (RPMI/FCS) (Gibco) supplemented with 1 mM sodium pyruvate, 2 mM L-glutamine, 200 U/ml of penicillin and 80 ng/ml of streptomycine. The GST-e4*/particle complexes were taken up in the same medium and incubated at 37° C. Aliquots were withdrawn at different times, and the percentage of GST-e4* combined with the particles was determined as above.

Uptake of GST-e4* by B lymphocyte lines and macrophage lines "in vitro":

Analysis of the uptake of GST-e4*, soluble or combined with the particles, was performed on a macrophage line ("Mono Mac 6", DSM ACC 124) and on a line of B lymphocytes immortalized with Epstein Barr virus (B/EBV). Cells (5×10$^5$/ml) in plate having 24 flat-bottomed wells (Falcon, Becton Dickinson, New Jersey) were incubated in RPMI/FCS in a moist atmosphere containing 5% of CO2, with different concentrations of GST-e4*, soluble or complexed with the particles (R=0.1). After 15 hours of incubation, the cells were harvested and washed twice in PBS. Free radioactivity was counted in the supernatant, in the washing liquid and in the cells resuspended in PBS. The results of counting correspond to the mean of three measurements. The percentage uptake for a given antigen concentration was expressed by the ratio of cell-bound radioactivity to total radioactivity.

Trypsic digestion of nanoparticle-associated antigen

Soluble [35S] GST-e4 and mixtures of the antigen with the different nanoparticles were incubated at room temperature with trypsin from bovine pancreas (Sigma) at a 1:600 mass ratio enzyme to substrate. After varying time intervals, the reactions (20 µl aliquots) were stopped by immediate freezing in liquid nitrogen. Prior to SDS-PAGE, samples were thawed and boiled in Laemmli sample buffer for 5 min. To ensure that particles did not inhibit the proteolytic activity of trypsin, mixtures containing 5 µg of the enzyme in the presence or absence of 3 mg particles per ml, were incubated with the enzyme substrate Chromozym-Try (Boehringer Manheim, France) according to the manufacturer's instructions. Trypsin activity was determined by the increase in absorbance at l=405 nm. Quantitation of the 82 kDa GST-e4 protein was determined by densitometric scanning of the Coomassie stained gel.

Immunofluorescence and confocal microscopy analyses

EBV-transformed B cells from donor "Be" and Burkitt lymphoma B cell line Raji were used. Cells were incubated in serum-free RPMI medium supplemented with 20 mM HEPES buffer pH 7.2 and 1 mg/ml bovine serum albumin (BSA) either at 37° C. or at 4° C. with 600 nM rhodamine-transferrin and/or 45 mg/ml FITC-AC for various incubation times. Then, cells were washed twice in cold PBS containing 1 mg/ml BSA (BSA-PBS), once in cold PBS alone, and fixed for 30 min at room temperature in PBS containing 3.7% paraformaldehyde and 30 mM sucrose. After a 10 min incubation time in 50 mM NH4Cl-PBS, three washes in BSA-PBS, and one in PBS, the cells were mounted on microscope slides in 25 mg/ml Dabco (1,4 diacylbicyclo (2.2.2) octane, Sigma St Louis, Mo.) 100 mg/ml mowiol (Calbiochem, La Jolla, Calif.), 25% (v/v) glycerol, 100 mM Tris-HCl pH 8.5. The samples were examined under a confocal microscope (Leica) attached to a diaplan microscope (Leitz) equipped with a double laser, Argon-Krypton. Serial optical sections were recorded at 0.5 mm intervals with a 63× lens. Photographs were taken on Ilford XP2 400 ASA.

Tests of proliferation of anti-IE1 TCD4+ clones:

The obtaining of clones of anti-IE1 TCD4+ lymphocytes and the analysis of their proliferation in the presence of autologous antigen presenting cells (APC) from CMV+ donors (Toulouse Blood Transfusion Centre) have been described previously (18). Briefly, $2 \times 10^4$ cells of a TCD4+ clone were incubated in plates having 96 round-bottomed wells (Falcon) with irradiated APC corresponding to $1 \times 10^5$ peripheral blood leukocytes (PBL) or $5 \times 10^4$ B/EBV lymphocytes, autologous or possessing MHC class II molecules of the same DR allotype. Cells were incubated in a final volume of 100 µl in RPMI containing 10% of a pool of human sera (RPMI/HS) (Laboratoires FANDRE, Ludres, France) and different dilutions of antigen, free or bound to the particles. Alternatively, soluble Ag and empty particles were added to cells at the time of use. The Ag/particle complexes were sterilized by irradiation. Three days later, the culture was labelled for 15 hours with 1 µCi per well of [$^3$H]thymidine (49 Ci/mmol, Amersham).

The proliferation of T clones is determined by measuring the incorporation of [3H]thymidine by the cells. The results expressed in cpm correspond to the mean of three concomitant experiments. The extracts of human astrocytomas (U373MG) transfected with IE genomic DNA (A2) or untransfected (A0) which had been used to generate the clones (18) were employed as positive and negative controls, respectively. Determination of the DR allotypes of the different donors was performed by PCR with specific oligonucleotide primers (Prof. Abbal, Centr. Immunol. Lab., Rangueil University Hospital Complex, Toulouse). The clones D11 and A3 originating from (DR3/DR4) and (DR8/DR7) indiviuals, respectively, were used.

2) Results

Characterization of the particles synthesized

The particle size was 80 nm, with a standard deviation of 20 nm. The level of charge was assayed at 0.8 mmol of hydroxycholine per gram of lyophilized nanoparticles. The samples tested were pyrogen-free.

Production of GST-e4

Expression of GST-e4 in *E. coli*

Expression of the GST-e4 fusion product in the bacterial lysates was tested in SDS-PAGE. Western blot analysis of the same samples with the antipeptide 85.75 and a human anti-CMV immune serum disclosed a specific reactivity associated with a protein of relative mass 82,000, in agreement with the mass expected for the GST-e4 fusion protein (FIG. 2). Autoradiography of the membrane disclosed a good incorporation of the radio-labelled residues in the 82 kDa protein disclosed by the antipeptide, under the cultured conditions described above.

Purification of GST-e4 by affinity chromatography

The bacterial lysates were subjected to chromatography on glutathione-Sepharose and analysed in SDS-PAGE. Bands of lower molecular mass comigrating with GST-e4 were visualized after Western blotting. These products copurified with GST-e4 probably result from degradation of the fusion protein, and contain the peptide sequence recognized by the antiserum 85.75. No signal was observed in the lane corresponding to GST. We have obtained reproducibly, and after a single passage through the column, 1 mg of GST-e4* with a specific activity of 400 mCi/mmol.

Combination of GST-e4* with the particles

Combination yield as a function of particle type

Particles (PSC, AC, SMBV) were incubated in the presence of radiolabelled GST-e4 (GST-e4*) in the proportion of 1 mg of protein for 10 mg of vector (R=0.1). The mean degrees of combination (20 tests) are of the order of 90% and are identical irrespective of the particles.

Saturation of the particles with GST-e4*

SMBVs (100 µg) were preincubated with increasing amounts of cold GST-e4 in an Ag/SMBV mass ratio ranging from 0.1 to 4 (R=0.1 to R=4). For each of these ratios, GST-e4* was added to the complexes, and the degree of combination of the hot protein with the vectors was determined by counting after ultrafiltration. FIG. 3 shows that the SMBVs are saturated with antigen when the Ag/SMBV mass ratio is equal to 2.

Stability of the GST-e4*/particle combination over time

GST-e4/particle complexes (R=0.1) were incubated in RPMI/FCS at 37° C. Analysis of the percentage of GST-e4 which remained combined with the particles after several days of incubation (FIG. 4) showed that the kinetics of release are identical for the three types of particles, with a greater slope over the first 24 hours. After 6 days of incubation, the level of GST-e4* combined is 85%, 80% and 70% with SMBV, AC and PSC, respectively. An SDS-PAGE analysis of the same samples followed by autoradiography enabled the protein combined with the particles to be visualized.

The antigen was stably associated to vectors and protected from proteolysis

The association efficiency of [35S]-GST-e4 ranged between 80 and 90% and was not dependent on the nature of cationised particles (PC, AC, SMBV), and When the antigen was incubated with anionic vectors (phosphated AC), no material was entrapped as expected from the acidic isoelectric point of GST-e4. This suggested that the nature of interactions between the antigen and particles was mainly ionic. In order to analyze the stability of GST-e4 association to vectors, the release of antigen from particles in culture conditions was determined over time. Over 6 days of incubation in complete medium (10% FCS), the kinetics of antigen release were identical for PC, AC, and SMBV, and the release never exceeded 30% for PC, 20% for AC and 15% for SMBV, respectively. We determined whether the antigen was protected from proteolysis through its association to vectors. To this end, soluble and complexed [35S]-GST-e4 antigen were submitted to digestion with trypsin and analyzed under SDS-PAGE. The gel was subsequently scanned for the presence of the 82 kDa product. Densitometric scanning showed that over two hours of incubation with the enzyme, 30% of the complexed antigen was accessible to proteolysis, whereas 85% in the soluble form was degraded (FIG. 8). The protective effect was not due to a direct enzyme inactivation by the particle since the kinetics of the enzyme activity using the "chromozyme Try" substrate was not affected by the presence of vectors (results not shown).

Uptake of GST-e4* by B lymphocyte and macrophage lines

GST-e4*/particle complexes (R=0.1) and the soluble GST-e4* protein were incubated in increasing amounts with macrophage and B/EBV lymphocyte lines. Kinetics of combination of the antigen preparations (0.6 $\mu$g/ml, R=0.1) with the cells showed an equivalent incorporation for a given sample type and for incubation times ranging from 10 min to 15 h (result not shown). FIGS. 5 and 6 show the percentage of antigen combined with the cells after 15 h of incubation as a function of the amount of complexed or soluble protein added. These figures show that, for B/EBV lymphocytes (FIG. 5) and macrophages (FIG. 6), the amount of soluble antigen combined with the cells is very low, even at high concentrations. As regards the uptake of the antigen as a function of the different types of particle, SMBVs enabled the highest incorporation yield (30%) to be obtained with both cell types. Yields of the order of 5 to 10% were obtained with PSCs and ACs, whereas they border on 1% with the soluble antigen.

Synthetic vectors are internalized by antigen presenting cells

To further investigate the mechanisms whereby the particles mediated the increase of the antigen uptake by cells, we analyzed their capacity to be internalized by APCs using confocal microscopy. EBV-transformed B cells from donor "Be" were incubated with fluorescein-labeled AC particles and rhodamine-transferrin for various times either at 4° C. or at 37° C. Then, cells were fixed, mounted and observed under a confocal microscope, as described in Materials and Methods. A Z series of optical sections was performed at 0.5 $\mu$m-increments. Measurements of fluorescein and rhodamine emissions from the same cell were acquired sequentially. Each image shows a medial optical cut of a representative cell,: fluorescein or rhodamine. Bar: 10 nm.

To this end, EBV-transformed B cells from donor "Be" were incubated with fluorescein-labelled AC particles for 19 h at 37° C. AC particles were found in intracellular vesicles, indicating that they were indeed inside the cells. To further study the mechanism responsible for synthetic vector internalization, we studied the kinetics of entry and we compared it with that of transferrin, used as a marker for receptor mediated endocytosis. Cells rapidly internalized transferrin, which was readily seen in intracellular vesicles. In contrast, fluorescent AC, SMBV or PC vectors were rarely seen inside the cells at incubation times shorter than three hours. Contrary to transferrin, fluorescent particles accumulated in large patches or caps on the cell surface. At 5, 7 and 19 h at 37° C., most of the cells displayed AC particles in intracellular compartments, although cellular organelles appeared to be different than those containing internalized transferrin. Similar results were obtained when cells from the Burkitt lymphoma B cell line Raji were studied.

Our data indicated that AC vectors were internalized by APC, and slowly accumulated in intracellular compartments. Moreover, both the kinetics of entry and their intracellular localization suggested that these particles followed an endocytosis pathway different from that of transferrin.

Specific CD4+ T cell response is enhanced in vitro after association of GST-e4 to nanoparticles We investigated whether the recombinant fusion protein GST-e4 either free or complexed to particles could be efficiently presented by APC to DR3 and DR8 restricted CD4+ T cell clones directed against IE1. The results of a representative proliferative response of the BeA3 clone, in the presence.

Of either HLA-matched PBL (FIG. 9) or B lymphocytes (FIG. 10) are shown. Similar results were obtained with the FzD11 clone. No proliferation of T cells was observed when either empty or GST-complexed particles were incubated either in the presence or in the absence of PBL (FIG. 9B) and B lymphocytes (FIG. 10B). In contrast, the capacity of particulate GST-e4 to stimulate the proliferation of clones was enhanced with any type of vectors. When PBL were used as APC this potentiating effect ranged from 5 to 25 fold. Remarkably, up to 25 fold less protein in the complexed form (AC) was required to elicit a proliferative response at a level similar to that obtained with free antigen (FIG. 9A). When B lymphocytes were used to present particulate antigen (FIG. 10A), the effect was in the same order of magnitude as that observed with PBL. In order to determine if binding of the antigen to particle was a prerequesite to this effect, empty AC and soluble antigen were added extemporaneously to cells. In these conditions, the enhancing effect was still observed but was much lower (2 fold), this might be ascribed to a quick association of the antigen to vectors at the moment of their introduction in culture wells, since total binding of GST-e4 to particles was achieved in 1 h at 4° C. (Material and Methods).

Further evidence of the advantages in using Biovectors in vaccine compositions is apparent from Examples 4–6 using the Biovectors (PSC and SMBV) prepared in accordance with Example 3.

Example 4 provides important evidence of the superiority of Biovectors in the mucosal administration of vaccines. In this experiment, a comparison was made between the intranasal (i.n.) administration of a monovalent split antigen of hemagglutinin (HA) and neuraminidase (N) prepared from viral membranes in cationic SMBVs with the intranasal and subcutaneous (s.c.) administration of antigen alone. The experiment demonstrates that the antigen administered i.n. in a Biovector is able to elicit a superior mucosal and seric response.

Thus, the total IgG, specific IgG and inhibitory hemagglutination were of the same order of magnitude when the antigen was administered i.n. in a SMBV compared to antigen administered s.c. alone. However, the antigen/SMBV formulation induces the production of circulating and secretory IgA, while the antigen alone administered s.c. or i.n., for practical purposes, did not.

Moreover the ratio of specific IgG to total IgG in the nasal washing was twice as high when the antigen was administered i.n. in a Biovector than when the antigen was administered alone s.c. A higher ratio means that the immune response is expected to be more specific and more protective. While not wishing to be bound by any theory, applicants believe that membrane antigens such as those used in this experiment are presented by the outer layer of the SMBV, creating a lipid surrounding favorable for presenting the antigen to the immune system.

The experiment described in Example 5 compares the effect of different formulations of the gp160 protein of HIV on the mucosal immune response of rabbits. The protein was administered with two formulations of a positively charged SMBV, a dispersed formulation and an resuspended formulation, i.e. a dispersed suspension that was freeze-dried and re-suspended. As a control, the protein was administered in combination with a potent mucosal adjuvant, subunit B of cholera toxin (CTB). In each of the three cases, a series of immunizations were made at thirty day intervals. The first two immunizations were vaginal, the second two immunizations were oral, and the final immunization was intramuscular.

The results showed that the SMBVs were at least as efficient as CTB in inducing specific IgA secretions in the vagina and in saliva ten days after the second vaginal administration, ($D_{40}$). The resuspended SMBVs induced a 50% increase of the IgAs when compared to formulations of the antigen with CTB or in dispersed SMBVs.

It should be noted that vaginal administration of the antigen induced secretion of specific IgAs in the saliva as well as in the vagina. Thus, the antigen, which entered the MALT (mucosal-associated lymphoid tissue) at the vaginal level, induced the secretion of IgAs in situ. In addition, the SMBV formulations were able to stimulate a robust IgA response in the saliva by entering the so-called "common mucosal immune system."

The experiment described in Example 6 compares the intranasal immunization of mice with influenza hemagglutinin in a control formulation with that of four formulations of SMBVs: dispersed and positively charged, dispersed and negatively charged, resuspended and positively charged, and resuspended and negatively charged. The effect of pre-loading and post-loading each Biovector formulation on the relative serum IgG titer after 28 days was measured. In addition, a comparison of the relative titer obtained by administering the pre-loaded SMBVs to animals that were awake with that obtained by administering the pre-loaded SMBVs to animals that were anesthetized was made.

As expected, the control subunit antigen without any carrier or adjuvant is not very immunogenic when administered intranasally to mice, either anesthetized or awake. Of the subgroups, the positively charged and dispersed SMBVs showed a significant improvement (by more than an order of magnitude) of the titer over those obtained with the antigen alone or other Biovector formulations. Both the pre-loaded and post-loaded SMBVs have generally comparable effects. This versatility of Biovectors can be of particular interest, allowing either a mixing of the active substance with the Biovector upon administration, or integration of the active substance with the Biovector prior to its use.

Surprisingly, the anesthetized animals did not show a significant increase in antibody titers, suggesting that the deposition, if any, of the antigen in the lower respiratory tract or the lung had little biological effect.

EXAMPLES

Example 3. Preparation of Biovectors

In the examples below, Biovectors, when labeled, are labeled before the phospholipidation process. When loaded with one (or more than one) biologically active compound, the loading occurs after the process of manufacturing the empty Biovector.

3(a). Preparation of anionic core Biovector (PSC-P1)

500 g of maltodextrine Glueidex (Roquette, Lestrem, France) are poured in a 10 liter reactor (TRIMIX) along with 2 liters of demineralized water. After solubilization at 4° C., 500 ml of sodium hydroxide (NaOH) 10M are added with mechanical stirring. When the temperature of the solution has stabilized at 4° C., 1700 ml of 10M NaOH and 283.3 ml of $POCL_3$ are added under controlled flow conditions. The cross linking reaction takes place with mechanical stirring during a 20 hour period. At the end of the 20 hour period, the reacting mixture is stirred an additional 15 minutes. A volume of 5 liters of demineralized water is added and the pH is adjusted to 7.0 by neutralization with glacial acetic acid. The hydrogel obtained is ground under high-pressure. At the end of this step, the mean diameter of the particles is approximately 60 nm. Further purification proceeds as follows: (I) microfiltration at 0.45 μm to eliminate larger particles, (ii) diafiltration at constant volume to eliminate smaller molecules (salts, fragments of polysaccharides, etc). The anionic polysaccharide cores (PSC) are then concentrated, added to sterile flasks, and stored at ~20° C.

3(b). Preparation of dispersed anionic light Biovector (SMBV-P2)

Anionic core Biovectors are prepared as described in Example 3(a), and labeled as described when necessary. Thawed cores are diluted in osmosed water in a glass flask at a concentration of 1 mg per milliliter (e.g. 250 mg of PSC/250 ml of water). The dispersion is stirred 5 to 10 minutes and homogenized in a high pressure homoginizer (RANNIE Lab) at 400 bars for 3 minutes. The suspension is warmed at 80° C. in a thermostated bath. The lipids of the future outer membrane (e.g. DPPC, DPPC/cholesterol, etc), in powder form, are added in a ratio of 0.3:1 (w/w) of the PSC mass (e.g. 75 mg of lipids for 250 mg of PSC). The lipids are mixed and solubilized in 2.5 ml of ethanol 95% (v/v). The homogenizer is warmed to 60° C. by closed water circulation. The ethanol solution of lipids is injected in the suspension of PSC at 80° C. and then homogenized at 450 bars for 25 minutes at 60° C. At the end of this step, the preparation is put in a glass container and free ethanol is eliminated from the SMBV preparation at reduced pressure. The resulting cationic or anionic SMBVs are filtered (0.2 μm) and stored.

3(c). Preparation of resuspended anionic light Biovector (SMBV-P3)

Anionic core (PSC-P1) and light (SMBV-P2) Biovectors are suspended in water at a concentration of 1.2 mg/ml, and then distributed in doses of 1 ml in cryovials especially designed for freeze-drying. The cryovials are placed on a freeze-dryer, (Dura dry, FT Systems), frozen at −30° C., and freeze dried in stages, first −10° C., then 0° C., and finally 10° C. during the primary drying, and 30° C. for the following step. Drying is usually achieved in 24 hours. The lyophilized Biovectors in each cryovial are rehydrated in 200 µl of PBS.

3(d). Preparation of cationic core Biovector (PSC-Q1)

500 mg of maltodextrine Glueidex (Roquette, Lestrem, France) are solubilized with 0.880 liters of water at 20° C., with stirring, in a thermoregulated reactor. Seven grams of $NaBH_4$ are added and mixed for 1 hour. 220 ml of NaOH 10M are added, followed by 30.25 ml of epichlorydrin (Fulka). After 12 hours of reaction, 382.3 g of glycidyltrimethlammonium chloride (Fulka) are introduced and the mixture is stirred for 10 hours. The resulting gel is diluted with 8 liters of demineralized water and the pH is adjusted to 7.0 by neutralization with glacial acetic acid. The hydrogel obtained is ground under high-pressure. The pressure used is 400 bars. At the end of this step, the mean diameter of the particles is approximately 60 nm. Further purification proceeds as follows: (I) microfiltration at 0.45 µm to eliminate larger particles, (ii) diafiltration at constant volume to eliminate smaller molecules (salts, fragments of polysaccharides). The cationic PSCs are then concentrated, sampled in sterile flasks and stored at ~20° C.

3(e). Preparation of dispersed cationic light Biovector (SMBV-Q2)

Cationic core Biovectors are prepared as described in Example 3(d), and labeled as described when necessary. Thawed cores are diluted in osmosed water in a glass flask at a concentration of 1 mg per milliliter (e.g. 250 mg of PSC/250 ml of water). The dispersion is stirred 5 to 10 minutes and homogenized (RANNIE Lab) at 400 bars for 3 minutes. The suspension is warmed at 80° C. in a thermostated bath. The lipids of the future outer membrane (e.g. DPPC, DPPC/cholesterol, etc), in powder form, are added in a ratio of 0.3:1 (w/w) of the PSC mass (e.g. 75 mg of lipids for 250 mg of PSC). The lipids are mixed and solubilized in 2.5 ml of ethanol 95% (v/v). A homogenizer is warmed to 60° C. by closed water circulation. The ethanol solution of lipids is injected in the suspension of PSC at 80° C. and then homogeneized at 450 bars during 25 minutes at 60° C. At the end of this step, the preparation is put in a glass container and free ethanol is eliminated from the light Biovector preparation at reduced pressure. Light cationic Biovectors are filtered (0.2 µm) and stored.

3(f). Preparation of resuspended cationic light Biovectors (SMBV-Q3)

Cationic core (PSC-Q1) and light (SMBV-Q2) Biovectors are suspended in water at a concentration of 1.2 mg/ml, and then distributed in doses of 1 ml in cryovials especially designed for freeze-drying. The cryovials are placed on a freeze-dryer, (Dura dry, FT Systems), frozen at −30° C., and free dried in stages, first −10° C., then 0° C., and finally 10° C. during the primary drying, and 30° C. for the following step. Drying is usually achieved in 24 hours. The lyophilized Biovectors in each cryovial are rehydrated in 200 µl of PBS.

3(g). Large scale preparation of dispersed light Biovectors

Modifications may be made to the procedures described in Examples 3(b) and 3(e) to assist in scaling up the procedures. The duration times of the high pressure homoginization steps are varied on the basis of the volume and the concentration of SMBVs to be prepared. The second high pressure homoginization step may be eliminated, and replaced by incubation of the SMBVs at 80° C. with stirring. The elimination of ethanol may be accomplished by means of diafiltration against water rather than at reduced pressure.

Example 4. Comparison of Intranasal Administration of a Monovalent Split of an Influenza Virus Antigen in Biovectors With Intranasal (i.n.) and Subcutaneous (s.c.) Administrations of HA Alone.

The antigen used in this study was a commercially available monovalent split of hemagglutinin (HA) and neuraminidase (N) prepared from viral membranes. The study was performed by administering 5 µg of the antigen in three groups of six BALB/c mice per group. Two groups received alone, one group i.n. and the other group s.c. The third group received antigen in a dispersed, positively charged Biovector (SMBV-Q) that had an amphiphilic layer (DPPC/chol in a ratio of 70:30) prepared in accordance with Example 3(e). The antigen was injected subcutaneously (s.c.) or administered intranasally (i.n.) at day zero and day twenty one. The antibody response was analyzed at day thirty five by ELISA and by inhibitory hemagglutination against Nib16. The results are shown in Table 4–1:

TABLE 4-1

Response to administration i.n. of antigen.

| Administration of Flu Vaccine | Total ELISA responses in sera | | | ELISA responses in nasal pharyngeal washings | |
|---|---|---|---|---|---|
| | IgG | IHA | IgA | Specific IgG | Specific IgA |
| subcutaneous | 350 000 | 320 | 0 | 64 | 0 |
| intranasal | 2 000 | 0 | 0 | 0 | 1,5 |
| intranasal in Disp. SMBV-Q | 145 000 | 240 | 581 | 48 | 128 |

Example 5. Comparison of Routes of Administration of gp160 of HIV With Biovectors.

Several successive immunizations at one month intervals were made in rabbits against the protein gp160 of HIV: two vaginal applications, two oral administrations and one intramuscular injection. Four female rabbits received five doses of 10 µg of gp160 of HIV, formulated in either:

(a) a solution containing the subunit B of the cholera toxin (CTB), the exotoxin of Vibrio cholerae, which is a potent mucosal adjuvant.

(b) a solution of positively charged, dispersed light Biovectors (disp. SMBV-Q)

(c) a solution of lyophilized, positively charged light Biovectors resuspended in PBS (resuspended light Biovectors—res. SMBV-Q).

Immunizations were made as follows: vaginal at day $D_0$ and $D_{30}$, oral at day $D_{60}$ and $D_{90}$ and intramuscular at day $D_{120}$.

Ten days after each immunization (days $D_{40}$, $D_{70}$, $D_{100}$ and $D_{130}$), the specific IgAs in the vagina mucosa and in the saliva were measured by ELISA. The results are shown in the Table below.

TABLE 5-1

| Vaginal administration of gp160 of HIV delivered by Biovectors | | |
|---|---|---|
| | IgAs in vagina at $D_{40}$ | IgAs in saliva at $D_{40}$ |
| gp160-CTB | 0.41 | 0.42 |
| gp160-disp SMBV-Q | 0.42 | 0.42 |
| gp160-res. SMBV-Q | 0.65 | 0.60 |

TABLE 5-2

| Oral Administration of gp160 of HIV delivered by Biovectors | | | |
|---|---|---|---|
| | IgAs in saliva | | IgAs in vagina |
| | $D_{70}$ | $D_{100}$ | $D_{100}$ |
| gp160-CTB | 0.42 | 0.38 | 0.28 |
| gp160-disp SMBV-Q | 0.47 | 0.35 | 0.29 |

Table 5–2 shows that, after the last vaginal administration, oral administration maintains the mucosal immunity at the same level.

Again, the Biovectors are as least efficient as CTB in maintaining specific IgA secretion by the vagina and the saliva.

TABLE 5-3

| Intramuscular Administration of gp160 of HIV Delivered by Biovectors | | |
|---|---|---|
| Day $D_{130}$ | IgAs in saliva | IgAs in vagina |
| gp160-CTB | 0.16 | 0.08 |
| gp160-disp SMBV-Q | 0.05 | 0.16 |

Table 5–3 shows that, at day $D_{130}$, the mucosal immunization does not persist. The intramuscular injection is not able to re-boost it.

The Biovector therefore appears to induce mucosal immunity when used to deliver antigens at the mucosal level. It is a vector of active compounds particularly adapted to mucosal administrations.

Example 6. Influenza Hemagglutinin Delivered Intranasally by Biovectors

Samples of four female mice were immunized at day $D_0$ and boosted at $D_{14}$ with 5 $\mu$g of hemagglutinin (HA) applied intranasally in 20 $\mu$l or 50 $\mu$l of a PBS solution or suspension, either alone or in an SMBV formulation. One group of animals was subjected to light ether anesthesia (*), while the others were awake. Administration of 20 $\mu$l on the outer nostrils of awake animals restricts the antigen to the upper respiratory tract. A volume of 50 $\mu$l directly into the nostrils of anesthetized animals results in deposition of at least part of the antigen in the lower respiratory tract and the lung, besides deposition in the nasal cavity.

Four different SMBVs were used: positively (SMBV-Q) and negatively (SMBV-P) charged light Biovectors, either resuspended (res) or dispersed (disp).

The influenza virus subunit antigen was either pre-loaded in the Biovectors (HA in SMBV) or simply post-loaded (HA+SMBV), i.e., admixed with them immediately before administration to the animals. The antigen alone was used as a control. The quality of the material used in the present study was equivalent to that for human vaccination purposes.

At day $D_{28}$, the mice were sacrificed. Serum samples were taken from the vena porta and antigen specific antibodies were measured in a direct enzyme-linked immunosorbent assay (ELISA). The results are shown in Table 6–1.

TABLE 6-1

Response to i.n. administration of HA in Biovectors. The numbers are serum IgG titers (geometric mean) determined as the reciprocal of the sample dilution that corresponds to an absorbance at 492 nm of 0.2 above background.

| | awake animals | | | anesthetized | |
|---|---|---|---|---|---|
| Administration of HA | HA | HA in SMBV | HA + SMBV | HA | HA in SMBV |
| alone | 100 | | | 200 | |
| disp SMBV-P | | 200 | 200 | | 60 |
| res SMBV-P | | 400 | 30 | | 30 |
| res SMBV-Q | | 10 | 20 | | 30 |
| disp SMBV-Q | | 2000 | 2000 | | 4000 |

BIBLIOGRAPHY (1) Alford C. A. and Britt W. J. (1990) Cytomegalovirus. In: Virology, Second Edition, (ed. B. N. Fields and D. M. Knipe et al.), Raven Press Ltd., New York.

(2) Rasmussen L. (1993) Progress in the development of a human Cytomegalovirus glycoprotein subunit vaccine. In S. Michelson, S. A. Plotkin eds. Multidisciplinary Approach to Understanding Cytomegalovirus Disease. Proceedings of the 4th international CMV workshop. Excerpta Medica. Amsterdam. 311–320.

(3) Liu Y-N., Klaus A., Kari B., Stinski M. F., Eckhardt J. and Gehrz R. C. (1991) The N-terminal 513 amino Acids of the Envelope Glycoprotein gB of Human Cytomegalovirus stimulates both B- and T-cell Immune responses in Humans. J. Virol. 65: 1644–1648.

(4) Gilbert M. J., Riddell S. R., Li C-H. and Greenberg P. (1993) Selective interference with class I Major histocompatibility complex presentation of the Major Immediate-Early Protein following Infection with Human Cytomegalovirus. J. Virol. 67: 3461–3469.

(5) Davignon J-L, Clément D., Alriquet J., Michelson S. and Davrinche C. (1994) Analysis of the proliferative T cell response specific for the Human Cytomegalovirus Protein IE1: Phenotype, Frequency and Variability. Scand. J. Immunol. 41: 247–255

(6) Fattal E, Couvreur P. and Puisieux F. (1993) Méthodes de préparation des liposomes [Methods of preparation of liposomes]. In: Les Liposomes. eds. INSERM, Paris, France.

(7) Ron Y., De Baestelier P., Gordon J., Feldman M. and Segal S. (1981) Defective induction of antigen-reactive proliferating T cells in B cell-deprived mice Eur. J. Immunol. 11: 964.

(8) Machy P. and Leserman L. (1993) Internalisation des molécules de surface cellulaire: implications sur le ciblage des liposomes [Internalization of cell surface molecules: implications for the targeting of liposomes]. In: Les Liposomes. eds. INSERM, Paris, France.

(9) LaFemina R. A., Pizzorno M. C., Mosca J. D. and Hayward G. S. (1989): Expression of the acidic nuclear immediate early protein (IE1) of the human cytomegalovirus in stable cell lines and its preferential association with metaphase chromosome. Virology. 172: 584–600.

(10) Guan K. and Dixon J. (1991) Eukaryotic proteins expressed in Escherichia coli: An improved thrombin cleavage and purification procedure of fusion proteins with glutathione S-transferase. Analyt. Biochem. 192: 262–267.

(11) Sambrook J., Fritsch E. and Maniatis T. (1989): Molecular cloning, a laboratory manual. Cold Spring Harbor Laboratory Press.

(12) Sanger F., Nicklen S. and Coulson A. R. (1977) DNA sequencing with chain terminating inhibitors. Proc. Natl. Acad. Sci. USA 74: 5463–5467.

(13) Marston F. A. O. (1986): The purification of eukaryotic polypeptides synthesized in Escherichia coli. Biochem. J. 240: 1–12.

(14) Smith D. B. and Johnson K. S. (1988) Single-step purification of polypeptides expressed in Escherichia coli as fusions with glutathione S-transferase. Gene 67: 31–40.

(15) Laemmli U. K. (1970): Cleavage of structural proteins during the assembly of the head of the bacteriophage T4. Nature 227: 680–685.

(16) Towbin H., Staehelin T. and Gordon J. (1979): Electrophoretic transfer of proteins from polyacrylamide gels to nitrocellulose sheets: Procedure and some applications. Proc. Natl. Acad. Sci. USA 76: 4350–4354.

(17) Stenberg R., Depto A. S., Fortney J. and Nelson J. (1989) Regulated expression of early and late RNAs and protein from the human cytomegalovirus immediate early gene region. J. Virology 63: 2699–2708.

(18) Davrinche C., Pasquier C., Cerutti M., Serradell L., Clement D., Devauchelle G., Michelson S. and Davignon J.-L. (1993) Expression of human Cytomegalovirus Immediate-early protein IE1 in insect cells: Splicing of RNA and recognition by CD4+ T-cell clones. Biochem. Biophys. Res. Com. 195: 469–477.

What is claimed is:

1. A method for increasing the immunogenicity of an antigen in an individual, the method comprising administering to the individual a composition consisting essentially of the antigen combined with a particulate vector, the particulate vector consisting essentially of a non-liquid hydrophilic core.

2. The method according to claim 1 wherein the non-liquid hydrophilic core is a matrix of naturally or chemically cross-linked polysaccharides or oligosaccharides.

3. The method according to claim 1 or claim 2 wherein the vectors are between 10 nm and 5 μm.

4. The method according to claim 1 or claim 2 wherein the size of the vector is between 25 nm and 200 nm.

5. The method according to claim 1 or claim 2 wherein the size of the vector is approximately 80 nm.

6. The method according to claim 1 or claim 2 wherein the antigen is an influenza antigen.

7. The method according to claim 6 wherein the influenza antigen comprises hemagglutinin.

8. The method according to claim 6 wherein the influenza antigen comprises a combination of hemagglutinin and neuraminidase.

9. The method according to claim 1 or claim 2 wherein cationic ligands are covalently bound to the non-liquid hydrophilic core.

10. The method according to claim 9 wherein the cationic ligands are quaternary ammonium groups, secondary amines or primary amines.

11. The method according to claim 1 or claim 2 wherein anionic ligands are covalently bound to the non-liquid hydrophilic core.

12. The method according to claim 11 wherein the anionic ligands are phosphates, sulphates, or carboxylates.

13. A method for increasing the immunogenicity of an antigen in an individual, the method comprising administering to the individual a composition consisting essentially of the antigen combined with a particulate vector, the particulate vector consisting essentially of a non-liquid hydrophilic core and a single outer layer.

14. The method according to claim 13 wherein the non-liquid hydrophilic core is a matrix of naturally or chemically cross-linked polysaccharides or oligosaccharides.

15. The method according to claim 13 or claim 14 wherein the single outer layer comprises a lipid.

16. The method according to claim 15 wherein the lipid comprises a fatty acid.

17. The method according to claim 16 wherein the fatty acid is a natural fatty acid bound to the non-liquid hydrophilic core by means of covalent bonds.

18. The method according to claim 15 wherein the lipid comprises a phospholipid.

19. The method according to claim 18 wherein the phospholipid comprises different types of phospholipids.

20. The method according to claim 13 or claim 14 wherein the vectors are between 10 nm and 5 μm.

21. The method according to claim 13 or claim 14 wherein the size of the vector is between 25 nm and 200 nm.

22. The method according to claim 13 or claim 14 wherein the size of the vector is approximately 80 nm.

23. The method according to claim 13 or claim 14 wherein the antigen is an influenza antigen.

24. The method according to claim 23 wherein the influenza antigen comprises hemagglutinin.

25. The method according to claim 23 wherein the influenza antigen comprises a combination of hemagglutinin and neuraminidase.

26. The method according to claim 13 or claim 14 wherein cationic ligands are covalently bound to the non-liquid hydrophilic core.

27. The method according to claim 26 wherein the cationic ligands are quaternary ammonium groups, secondary amines or primary amines.

28. The method according to claim 13 or claim 14 wherein anionic ligands are covalently bound to the non-liquid hydrophilic core.

29. The method according to claim 28 wherein the anionic ligands are phosphates, sulphates, or carboxylates.

* * * * *